US010896766B2

(12) United States Patent
Shaya

(10) Patent No.: US 10,896,766 B2
(45) Date of Patent: *Jan. 19, 2021

(54) SYSTEM, METHOD AND APPARATUS FOR REAL-TIME ACCESS TO NETWORKED RADIOLOGY DATA

(71) Applicant: Fawzi Shaya, Wixom, MI (US)

(72) Inventor: Fawzi Shaya, Wixom, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/990,074

(22) Filed: Aug. 11, 2020

(65) Prior Publication Data

US 2020/0373020 A1 Nov. 26, 2020

Related U.S. Application Data

(63) Continuation of application No. 16/818,243, filed on Mar. 13, 2020, now Pat. No. 10,777,326, which is a (Continued)

(51) Int. Cl.
*G16H 80/00* (2018.01)
*G16H 40/20* (2018.01)
(Continued)

(52) U.S. Cl.
CPC ............ *G16H 80/00* (2018.01); *A61B 5/0022* (2013.01); *A61B 5/746* (2013.01); *G06F 3/0482* (2013.01);
(Continued)

(58) Field of Classification Search
CPC ........ G16H 10/60; G16H 10/65; G16H 30/20; G16H 40/67; G16H 40/63; G16H 30/40;
(Continued)

(56) References Cited

U.S. PATENT DOCUMENTS 5,961,446 A 10/1999 Beller et al.
5,987,519 A 11/1999 Peifer et al.
(Continued)

FOREIGN PATENT DOCUMENTS

WO WO-01/47418 A1 7/2001

OTHER PUBLICATIONS

Bluegiga Technologies "Bluetooth® Health Device Profile" Aug. 2009, https://www.semiconductorstore.com/pdf/NewSite/Bluegiga_/Bluegiga <https://www.semiconductorstore.com/pdf/NewSite/Bluegiga/Bluegiga> Bluetooth Health Device Profile.pdf (Year: 2009).

(Continued)

*Primary Examiner* — Joseph D Burgess
(74) *Attorney, Agent, or Firm* — Honigman LLP

(57) ABSTRACT

A method for generating DICOM images as part of a real-time virtual medical consultation includes receiving, by a handheld patient device associated with a patient, a DICOM image associated with the patient generated by a diagnostic device, encrypting, by the handheld patient device, the DICOM image and linking the encrypted DICOM image to a unique patient identifier associated with the patient, wherein the handheld patient device is one of a tablet computer and a smartphone, and transmitting, by the handheld patient device, the encrypted DICOM image to a server configured to provide a DICOM viewer option within a secure telemedicine platform accessible by a medical professional and executed by the server.

20 Claims, 25 Drawing Sheets

Related U.S. Application Data continuation of application No. 16/209,064, filed on Dec. 4, 2018, now Pat. No. 10,629,311, which is a continuation-in-part of application No. 15/784,876, filed on Oct. 16, 2017, now abandoned, which is a continuation-in-part of application No. 15/158,007, filed on May 18, 2016, now abandoned, which is a continuation-in-part of application No. 13/165,052, filed on Jun. 21, 2011, now abandoned.

(60) Provisional application No. 61/369,461, filed on Jul. 30, 2010.

(51) Int. Cl.
*A61B 5/00* (2006.01)
*H04W 12/00* (2009.01)
*H04L 29/06* (2006.01)
*G06F 3/0482* (2013.01)

(52) U.S. Cl.
CPC .......... *G16H 40/20* (2018.01); *H04L 63/0428* (2013.01); *H04W 12/003* (2019.01)

(58) Field of Classification Search
CPC ........ G16H 80/00; G06Q 50/22; G06Q 50/24; G06F 19/00; G06F 19/321; G06F 19/3418
See application file for complete search history.

(56) References Cited

U.S. PATENT DOCUMENTS

| | | |
|---|---|---|
| 5,997,476 A | 12/1999 | Brown |
| 6,038,469 A | 3/2000 | Karlsson et al. |
| 6,064,968 A | 5/2000 | Schanz |
| 6,112,224 A | 8/2000 | Peifer et al. |
| 6,366,871 B1 | 4/2002 | Geva |
| 6,369,847 B1 | 4/2002 | James et al. |
| 6,409,660 B1 | 6/2002 | Sjoqvist |
| 6,610,010 B2 | 8/2003 | Sjoqvist |
| 6,640,239 B1 | 10/2003 | Gidwani |
| 6,820,057 B1 | 11/2004 | Loch et al. |
| 7,158,861 B2 | 1/2007 | Wang et al. |
| 7,222,054 B2 | 5/2007 | Geva |
| 7,232,220 B2 | 6/2007 | Franz et al. |
| 7,257,158 B1 | 8/2007 | Figueredo et al. |
| 7,283,153 B2 | 10/2007 | Provost et al. |
| 7,412,396 B1 | 8/2008 | Haq |
| 7,425,977 B2 | 9/2008 | Sakai |
| 7,520,611 B2 | 4/2009 | Franz et al. |
| 7,618,368 B2 | 11/2009 | Brown |
| 7,624,028 B1 | 11/2009 | Brown |
| 7,650,291 B2 | 1/2010 | Rosenfeld et al. |
| 7,657,444 B2 | 2/2010 | Yu |
| 7,761,261 B2 | 7/2010 | Shmueli et al. |
| 7,761,312 B2 | 7/2010 | Brown |
| 7,815,282 B2 | 10/2010 | Hibbard et al. |
| 9,210,200 B1 | 12/2015 | Chapweske et al. |
| 2001/0044586 A1 | 11/2001 | Ferek-Petric |
| 2002/0065682 A1 | 5/2002 | Goldenberg |
| 2002/0091659 A1 | 7/2002 | Beaulieu et al. |
| 2002/0118809 A1 | 8/2002 | Eisenberg |
| 2003/0028399 A1 | 2/2003 | Davis et al. |
| 2003/0069752 A1 | 4/2003 | LeDain et al. |
| 2004/0078219 A1 | 4/2004 | Kaylor et al. |
| 2005/0246185 A1 | 11/2005 | Brown |
| 2006/0036134 A1 | 2/2006 | Tarassenko et al. |
| 2006/0074709 A1 | 4/2006 | McAllister |
| 2006/0122466 A1 | 6/2006 | Nguyen-Dobinsky et al. |
| 2006/0143043 A1 | 6/2006 | McCallie et al. |
| 2006/0173267 A1 | 8/2006 | Chiang et al. |
| 2006/0271400 A1 | 11/2006 | Clements et al. |
| 2007/0016449 A1 | 1/2007 | Cohen et al. |
| 2007/0073520 A1 | 3/2007 | Bleines |
| 2007/0100666 A1 | 5/2007 | Stivoric et al. |
| 2007/0130287 A1 | 6/2007 | Kumar et al. |
| 2007/0192910 A1 | 8/2007 | Vu et al. |
| 2008/0095079 A1 | 4/2008 | Barkley et al. |
| 2008/0113621 A1 | 5/2008 | Parthasarathy |
| 2008/0267401 A1 | 10/2008 | Ferren et al. |
| 2008/0275311 A1 | 11/2008 | Haq |
| 2009/0012373 A1 | 1/2009 | Raij et al. |
| 2009/0093688 A1 | 4/2009 | Mathur |
| 2009/0112070 A1 | 4/2009 | Lin et al. |
| 2009/0146822 A1 | 6/2009 | Soliman |
| 2009/0149767 A1 | 6/2009 | Rossetti |
| 2009/0167842 A1 | 7/2009 | Sandhu |
| 2009/0240525 A1 | 9/2009 | Sadler et al. |
| 2009/0264712 A1 | 10/2009 | Baldus et al. |
| 2009/0313076 A1 | 12/2009 | Schoenberg |
| 2010/0030580 A1 | 2/2010 | Salwan |
| 2010/0079281 A1 | 4/2010 | Drake |
| 2010/0128104 A1 | 5/2010 | Fabregat et al. |
| 2010/0137693 A1 | 6/2010 | Porras et al. |
| 2010/0205541 A1 | 8/2010 | Rapaport et al. |
| 2010/0325209 A1 | 12/2010 | Thapa |
| 2011/0010200 A1 | 1/2011 | Firozvi et al. |
| 2011/0015494 A1 | 1/2011 | Spaulding |
| 2011/0106557 A1 | 5/2011 | Gazula |
| 2011/0126127 A1 | 5/2011 | Mariotti et al. |
| 2011/0145016 A1* | 6/2011 | Eshraghian ............ G16H 30/20 705/3 |
| 2014/0244296 A1 | 8/2014 | Linn et al. |
| 2015/0149565 A1 | 5/2015 | Ahmed |
| 2016/0037057 A1 | 2/2016 | Westin et al. |
| 2019/0356479 A1 | 11/2019 | Grimme |

OTHER PUBLICATIONS

"Application of Portable CDA for Secure Clinical-document Exchange", Huang, et al., J Med Syst (2010) 34:531-539 (Year: 2010).

* cited by examiner

SYSTEM, METHOD AND APPARATUS FOR REAL-TIME ACCESS TO NETWORKED RADIOLOGY DATA

CROSS-REFERENCE TO RELATED APPLICATIONS

This application claims priority to U.S. Provisional Patent Application No. 61/369,461, filed Jul. 30, 2010, U.S. Non-provisional patent application Ser. No. 13/165,052, filed Jun. 21, 2011, U.S. Non-provisional patent application Ser. No. 15/158,007, filed May 18, 2016, U.S. Non-provisional patent application Ser. No. 15/784,876, filed Oct. 16, 2017, U.S. Non-provisional patent application Ser. No. 16/209,064, filed Dec. 4, 2018, and U.S. Non-provisional patent application Ser. No. 16/818,243, filed Mar. 13, 2020, the contents of each of which are hereby incorporated by reference in their entirety.

FIELD

The disclosure generally relates to remote medical diagnostic and monitoring systems and solutions in which a physician conducts an examination of a remotely located patient, and more specifically, to a system and method for providing a second opinion option and biosensor monitoring.

BACKGROUND

Access to medical care providers remains a challenge for many patient populations, both due to cost and lack of geographic proximity. Patient populations in rural areas, especially those in third world countries, will likely find themselves without adequate numbers of local treating physicians for decades to come. Many patients are house-bound and cannot easily travel to a medical clinic. In addition, certain types of specialists (e.g., neurologists) are often in short supply, leaving some patient populations underserved.

Telemedicine systems have been proposed as a way of remotely diagnosing and treating patients using telephonic communications. However, known systems typically suffer from several drawbacks. First, many of them lack adequate safeguards to protect the confidentiality of patient medical information. In the United States, the Health Insurance Portability and Accountability Act of 1996 ("HIPAA") requires entities exchanging health care information to enact appropriate safeguards to protect the confidentiality of electronically transmitted patient information. Many prior telemedicine systems do not allow patients and physicians to communicate in real time in a manner that protects their communications from third parties.

In addition, many known telemedicine systems lack a mechanism for conveniently and securely transmitting patient information, such as real time access to networked/ remote radiology images and even simultaneous videoconferencing related to such images. Thus, a need has arisen for a system and method for secure HIPAA complaint data access by a health professional particularly related to radiology data, such as DICOM images and the like which address the foregoing issues.

SUMMARY

A method for generating DICOM images as part of a real-time virtual medical consultation includes receiving, by a handheld patient device associated with a patient, a DICOM image associated with the patient generated by a diagnostic device, encrypting, by the handheld patient device, the DICOM image and linking the encrypted DICOM image to a unique patient identifier associated with the patient, wherein the handheld patient device is one of a tablet computer and a smartphone, and transmitting, by the handheld patient device, the encrypted DICOM image to a server configured to provide a DICOM viewer option within a secure telemedicine platform accessible by a medical professional and executed by the server. The handheld patient device may include a memory and a processor configured to execute the steps of encrypting, linking, and transmitting the DICOM image. In some implementations, the diagnostic device is configured to transmit the DICOM image to the processor of the handheld patient device via one of a wireless connection and a wired connection. The diagnostic device may include a wireless transmitter configured to transmit the DICOM image to the processor of the handheld patient device. The DICOM image may be encrypted using a hypertext transfer protocol secure method. The diagnostic device may be one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

A system includes a handheld patient device associated with a patient, the handheld patient device being one of a tablet computer and a smartphone, and the handheld patient device comprising data processing hardware, and memory hardware in communication with the data processing hardware, the memory hardware storing instructions that when executed on the data processing hardware cause the data processing hardware to perform operations comprising receiving a DICOM image associated with the patient generated by a diagnostic device, encrypting the DICOM image and linking the encrypted DICOM image to a unique patient identifier associated with the patient, and transmitting the encrypted DICOM image to a server configured to provide a DICOM viewer option within a secure telemedicine platform accessible by a medical professional and executed by the server. In some implementations, the diagnostic device is configured to transmit the DICOM image to the processor of the handheld patient device via one of a wireless connection and a wired connection. The diagnostic device may include a wireless transmitter configured to transmit the DICOM image to the processor of the handheld patient device. The DICOM image may be encrypted using a hypertext transfer protocol secure method. The diagnostic device may be one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

A method for viewing DICOM images as part of a real-time virtual medical consultation using at least one DICOM viewer includes receiving, by a server, a DICOM image associated with a patient generated by a diagnostic device and transmitted to a handheld patient device associated with the patient, the handheld patient device being one of a tablet computer and a smartphone, and the handheld patient device being configured to (i) encrypt the DICOM image, (ii) link the encrypted DICOM image to a unique patient identifier associated with the patient, and (iii) transmit the encrypted DICOM image to the server, providing, by the server, a DICOM viewer option within a secure telemedicine platform accessible by a medical professional and executed by the server, supplying, via the secure telemedicine platform, a remote DICOM image database linked to a patient record based on the patient identifier, providing, via the DICOM viewer option, choices so that the medical professional has the ability to choose which type of DICOM image they desire or need, wherein the choices are selected from a list consisting of a synchronous review, an asynchronous review, an image review, a video review, and a stacked series review, and transferring, by the server, the encrypted DICOM image from the remote DICOM image database to the secure telemedicine platform to be viewable by the medical professional based on the selected image choice.

In some implementations, the method includes providing concurrent videoconferencing capability between a caller and a callee using WebRTC functionality. The method may include providing, by the server, a second opinion platform accessible by a second medical professional and executed by the server. The method may include providing, via the second opinion platform, choices so that the second medical professional has the ability to choose which type of DICOM image they desire or need, wherein the choices are selected from a list consisting of a synchronous review, an asynchronous review, an image review, a video review, and a stacked series review. The second medical professional may be remote from the medical professional. The method may include displaying, by a medical professional device associated with the medical professional, the secure telemedicine platform on a display of the medical professional device. The medical professional device may be one of a tablet computer and a smartphone. The method may include decrypting, by a medical professional device associated with the medical professional, the encrypted DICOM image. The diagnostic device may be one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

Other aspects and features of the embodiments herein will become apparent to those ordinarily skilled in the art upon review of the following description of specific embodiments in conjunction with the accompanying figures.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 15 illustrates an exemplary Login in screen to access an exemplary application to view DICOM records and the like.

FIG. 21 illustrates an alternate exemplary Login in screen with a graphical user interface screen to access an exemplary applications including an application to view DICOM records and the like.

DETAILED DESCRIPTION

Described herein are systems, methods and apparatuses for performing virtual medical examinations. The systems, methods and apparatuses generally involve the secure transmission of patient diagnostic information by a patient remotely located from a treating physician and the secure retrieval and viewing of the data by the physician. The systems, methods and apparatuses also generally involve secure videoconferencing to allow the physician to remotely conduct a medical examination in real-time, thereby allowing the physician to provide health instruction information by, for example directing the examination, providing therapeutic instructions and any other instructions to the patient.

Figure 1:
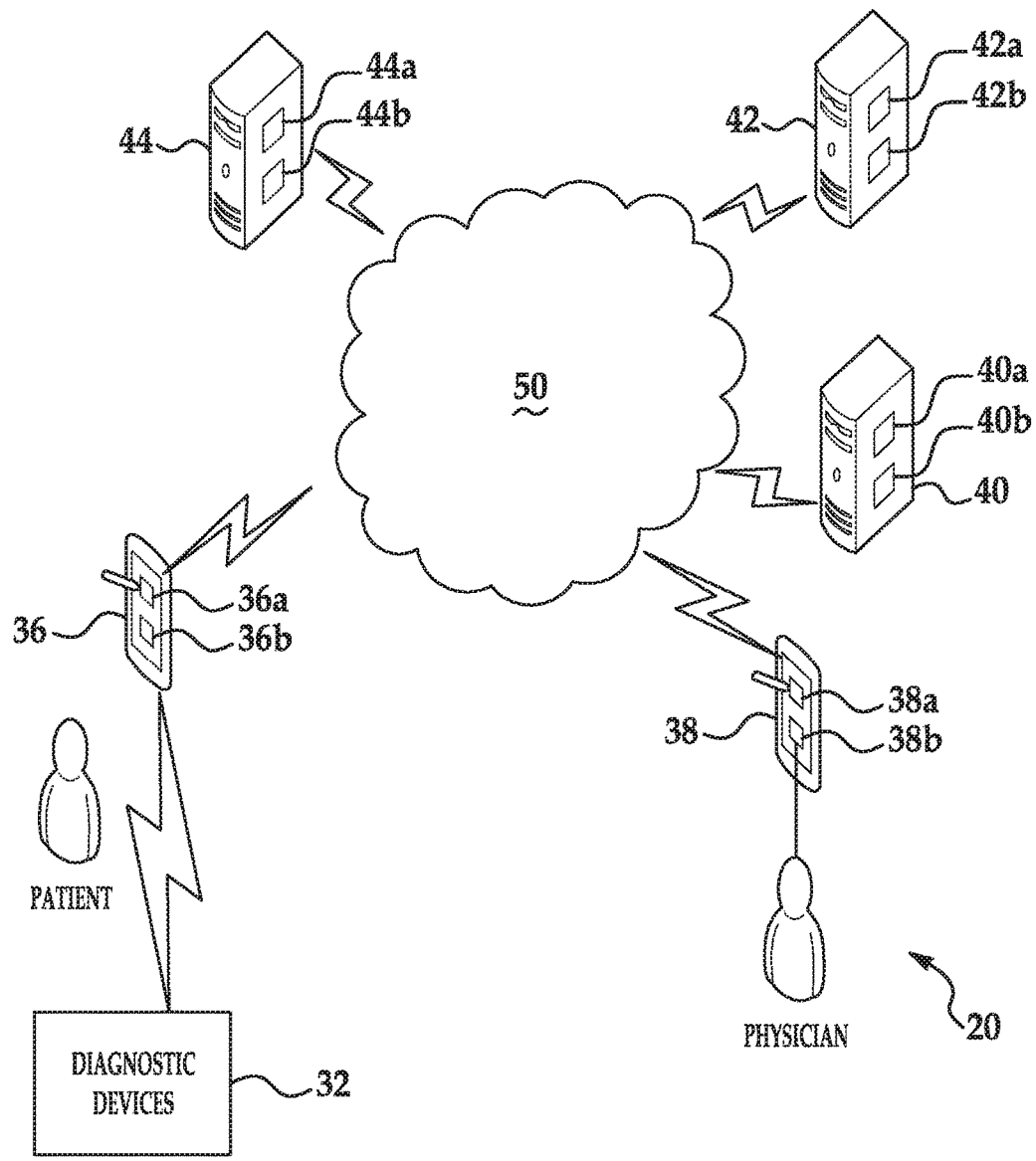
FIG. 1 is a diagram of a system for performing virtual medical examinations in accordance with one embodiment.

Referring to FIG. 1, a virtual medical examination system 20 is depicted. The system can include one or more diagnostic devices 32 that are configured to generate patient diagnostic information, a remote patient device 36, a physician device or healthcare provider device 38, a patient records server 40, a videoconferencing server 42 and a remote content manager server 44. Diagnostic devices 32, remote patient device 36, physician device 38, patient records server 40, videoconferencing server 42 and remote content manager server 44 can all be connected either directly or indirectly via a network 50.

Remote patient device 36, physician device 38, patient records server 40, videoconferencing server 42 and remote content manager server 44 may each be a computer having an internal configuration of hardware including a processor such as a central processing unit (CPU) and a memory. Accordingly, remote patient device 36 can have a CPU 36 a and a memory 36 b, physician device 38 can have a CPU 38 a and a memory 38 b, patient records server 40 can have a CPU 40 a and a memory 40 b, videoconferencing server 42 can have a CPU 42 a and a memory 42 b and remote content manager server 44 can have a CPU 44 a and a memory 44 b. CPUs 36 a, 38 a, 40 a, 42 a and 44 a can be a controller for controlling the operations of patient device 36, physician device 38, patient records server 40, videoconferencing server 42 and remote content manager server 44, respectively. CPUs 36 a, 38 a, 40 a, 42 a and 44 a can each be connected to memories 36 b, 38 b, 40 b, 42 b and 44 b, respectively, by, for example, a memory bus. Memories 36 b, 38 b, 40 b, 42 b and 44 b can store data and program instructions which are used by CPUs 36 a, 38 a, 40 a, 42 a and 44 a, respectively. Other suitable implementations of patient device 36, physician device 38, patient records server 40, videoconferencing server 42 and remote content manager server 44 are possible. For example, in one embodiment, patient records server 40, videoconferencing server 42 and remote content manager server 44 can be integrated into one server.

Exemplary diagnostic devices 32 include electrocardiographs (ECG), pulse oximeters, blood pressure cuff, spirometers, sphygmomanometers, weight scales, stethoscopes, blood chemistry analyzers, microscopes, ultrasounds probes, glucometers, horoscope, PT/INR, medication station, and the like. In clinic or visiting nurse peripherals can include abdominal probes, vascular access probes, endocavity probes, ophthalmology probe, proscope, thermometer, remotely controlled 360 degree high definition cameras, and the like. The diagnostic devices 32 can include a patient diagnostic information wireless transmitter for transmitting patient diagnostic information to a remote patient device 36. Communications between diagnostic devices 32 and patient device 36 can be wired and/or wireless.

Wireless communications between diagnostic devices 32 and patient device 36 may be provided using various protocols and other wireless technologies, including 3G and 4G wireless technologies and the IEEE series of wireless technologies. More particularly, wireless communications may take place over a CDMA, EDGE, EV-DO, GPRS, GSM, UMTS, W-CDMA, or a 1×RTT network as well as an IEEE 802.11 (WIFi), 802.15 (Bluetooth and Zigbee), 802.16 (WiMax) or 802.20 (MBWA) network. In the example shown in FIG. 1, wireless communications diagnostic devices 32 and patient devices 36 will take place using Bluetooth technology, but the embodiments disclosed herein are not to be limited to Bluetooth.

Bluetooth communications have certain features that can be beneficial in many implementations of system 20, including a lack of wires, security features such as secure simple device pairing and adaptive frequency hopping, and an effective device to device transmission range of up to about 300 feet. Using the Bluetooth protocol, suitable diagnostic devices 32 can be identified and paired with the remote patient work stations 36. Suitable Bluetooth-enabled diagnostic devices 32 can be supplied by QRS Diagnostics of Plymouth, Minn.

In other embodiments, rather than communications between diagnostic devices 32 and patient device 36 occurring directly, communications may occur directly via, for example, a local wireless signal gateway (not shown) The wireless signal gateway can be connected to network 50 and is generally in close proximity to diagnostic devices 32 at the time of their transmission of diagnostic information. In one embodiment, the wireless signal gateway is a Bluetooth-enabled wireless signal gateway that may operate external to the patient device 36 hardware as a separate entity or can be integrated into patient devices 36 to allow for long-range transmission of patient diagnostic information to an internet server (not separately shown in FIG. 1), and ultimately, to patient records server 40. One suitable Bluetooth internet gateway that may be used is the Gigaset-One Bluetooth Gateway supplied by Siemens, and the like such as a gateway sold under the tradename DELL or INTEL.

When communication between diagnostic device 32 and patient device 36 is via a wireless protocol, diagnostic device 32 and patient device 32 can be within a suitable distance from one another to permit communication. For example, in one embodiment, diagnostic device 32 and patient device 32 are no more than 90 feet one another although other suitable distances are possible. Because diagnostic devices 32 have a relatively limited transmission radius, the transmission of patient diagnostic information from diagnostic devices 32 to patient devices 36 need not be encrypted. However, patient diagnostic information transmitted from diagnostic devices 32 to patient records server 40 can be encrypted to prevent undesired access by other users of network 50. One encryption method includes https (hypertext transfer protocol secure). However, other encryption methods may be used. In one embodiment, wireless signals can secured via unique user identifiers for patient diagnostic peripheral devices 32.

In one implementation, the diagnostic devices 32 and patient devices 36 utilize the Bluetooth Health Device Profile for transmitting medical data. The Bluetooth Health Device Profile has been standardized by Bluetooth SIG, the industrial association for Bluetooth manufacturers. The Health Device Profile enables a range of additional functions such as exact chronological synchronization of several Bluetooth connected medical sensors or the option of transferring different medical data in parallel via a Bluetooth interface which is necessary when several diagnostic devices generate patient diagnostic information simultaneously. The Health Device Profile consists of one part that specifies transfer protocols used for medical data in the Bluetooth stack and another part that describes the structure of the actual medical data.

Patient records server 40 is connected to network 50 and can include a number of patient data files stored in a computerized database. The files may be organized by a variety of methods. However, in one implementation, each patient's files are associated with patient identification data, which can be a unique identifier, such as a numeric or alphanumeric identifier. The patient identifier allows a physician or any other health care provider (e.g. nurse, health care administrator, pharmacist surgeon etc.) to retrieve specific data for a desired patient. Patient diagnostic information transmitted from diagnostic devices 32 can be transmitted in association with a patient identifier so that patient diagnostic information received by patient records server 40 is associated with the specific patient for whom the diagnostic data was generated.

Network 50 may take a variety of forms such as a local area network, wide area network, or the Internet. When network 50 is, for example, the Internet medical examinations can be conducted between physicians and patients who are geographically situated at long distances from one another. In the case where network 50 is the internet, patient records server 40 is referred to as a patient records internet server. In such cases, patient records internet server 40 can be assigned a unique internet protocol address to which wireless signal transmissions from patient device 36 are directed when patient diagnostic information is generated by diagnostic devices 32.

Additionally, other networks can be interfaced with or completely replace network 50. For example, when physician device 38 is a handheld device such as a mobile phone, PDA, smart phone or any other suitable handheld device, network 50 can be a mobile communications network and can include one or more base stations (e.g. macrocell, femtocell, microcell, picocell, etc.). Physician device 38 can send communications to network 50 via the mobile communications network or other transmitting/receiving tower. For example, radio waves can be used to transfer signals between physician device 38 through one or more base stations in the mobile communications network, which can them transmit the communications to network 50. Physician device 38 may also communicate in any other suitable manner For example, in one embodiment, physician device may communicate via satellite. Further, for example, physician device 38 can connect directly to network 50 (e.g. via 3 g or 4 g services).

When physician device 38 is a handheld device, it can include a subscriber identity module (SIM) card, which can be equipped with encryption/decryption programming. This encryption/decryption programming can be used to authenticate the handheld device and can be in addition to the encryption and decryption of diagnostic information and health instruction information as will be discussed in more detail below. In some embodiments, the SIM card can be used to perform the encryption/decryption of the diagnostic information and health instruction information.

The SIM card can be in a form that is removable by the user, which can make it possible to carry mobile subscription information and data through different types and generations of handheld devices. Alternatively, the SIM card can be integrated into the handheld device. The SIM card can, for example, contain a microchip that houses a processor (e.g. microprocessor) and a memory. The memory can have instructions stored thereon, that when executed by the processor encrypt voice and data transmissions, which can assist in preventing third parties from intercepting transmissions. The SIM, as discussed previously, can identify the user to the mobile communications network as a legitimate user. Each SIM card can be equipped with an additional memory such as EEPROM (Electrically Erasable Programmable Read-Only Memory), which can contain additional information about the device. For example, EEPROM can store an IMSI (International Mobile Subscriber Identification), a PIN (Personal Identification Number), an international access entitlement, a priority class, and subscriber information.

As indicated in FIG. 1 virtual medical examination system 20 includes a physician device 38, which can be a hand-held computing device with a visual display. Device 38 can be programmed to allow the physician to access, retrieve, decrypt, and view patient diagnostic information from patient records server 40. Device 38 can be connected to network 50. In one embodiment, physician device 38 is wirelessly connected to the internet and configured to generate the IP address of patient record server 40 for the retrieval of patient diagnostic information. Physician device 38 can also be programmed to decrypt patient diagnostic information received from patient records server 40 via network 50 so the data can be displayed on physician device 38. Thus, the networking of physician device 38 with patient records server 40 and diagnostic devices 32 allows for the secure transmission of patient diagnostic information to patient record server 40 and the secure retrieval of patient diagnostic information from patient record server 40 by a physician. Patient record server 40 may be programmed to require one or more passwords or other sign-in credentials to verify the identity of the physician and ensure that access to patient diagnostic information is appropriately limited to authorized individuals. The transmission of patient diagnostic information to patient records server 40 and the subsequent retrieval of the data from patient records server 40 by a physician can occur in real-time.

Virtual medical examination system 20 can also be configured to allow a patient and physician to conduct video conference calls. In one implementation, system 20 is configured to allow a patient and physician to conduct secure, encrypted video conference calls that cannot be monitored or accessed by unauthorized third parties. In one example, the encryption provides for HIPAA compliant transmission of patient information. In another implementation, multiple authorized parties may participate in the video conference calls, thereby allowing multiple physicians (who may be remote from one another and from the patient) to collaborate and/or jointly conduct an examination of the patient.

In the illustrative example of FIG. 1, a videoconferencing server 42 is provided which allows a patient and physician to conduct a secure encrypted video conference call over network 50. A "secure" videoconference server includes features that prevent or minimize the likelihood that third parties will be able to intercept information transmitted from one party to another during the videoconference. Such interception is sometimes referred to as a "man in the middle attack" or "packet sniffing." In some embodiments, network 50 is the Internet, in which case the videoconferencing server 42 may be referred to as a videoconferencing internet server. In one embodiment, the patient speaks into a microphone (which may be provided on device 36), and stands in the field of view of a camera (which may also be provided on device 36) to generate voice and video data. The voice and video data is encrypted, for example by using https, and transmitted to video conferencing server 42 via network 50. Https can create a secure channel over an unsecure network, such as the internet. The trust inherent in HTTPS is based on major certificate authorities which come pre-installed in browser software, which allows users to confirm the security of the connection if (1) the user trusts that their browser software correctly implements HTTPS with correctly pre-installed certificate authorities; (2) the user trusts the certificate authority to vouch only for legitimate websites without misleading names; (3) the website provides a valid certificate (an invalid certificate shows a warning in most browsers), which means it was signed by a trusted authority; (4) the certificate correctly identifies the website; and (5) either the intervening hops on the Internet are trustworthy, or the user trusts that the protocol's encryption layer (TLS or SSL) is unbreakable by an eavesdropper.

A physician can use device 38 to receive voice and video data from the patient. The voice and video data is transmitted in encrypted form, from videoconferencing server 42 to device 38. Device 38 includes a display screen for viewing video images of the patient and a speaker for listening to voice communications from the patient. The physician speaks into a microphone (which may be provided on device 38) and stands in the field of view of a camera (which may also be provided on device 38) to generate voice and video data. The voice and video data are encrypted by device 38 and transmitted to video conferencing server 42 via network 50. The encrypted voice and video data is then received and decrypted by patient device 36 via network 50. Patient device 36 can include a visual display for viewing images of the physician and a speaker for listening to voice communications from the physician.

Videoconferencing server 42 can be a computer server that is connected to network 50. Video conferencing server 42 can be a video conferencing internet server, as in the case where network 50 is the internet. Suitable servers are supplied by Visual Systems Group, Inc., Radvision Ltd., and Tandberg. In one embodiment, a video conference call between a patient and physician is conducted using a single, secured TCPHP connection. In another embodiment, videoconferencing server 42 is configured to allow multiple parties to participate in a secure virtual medical examination. This option is particularly useful for situations in which a primary physician and a secondary physician (e.g., a consultant or specialist) are geographically remote from one another and from the patient In one example, a virtual conference room is provided which allows for a multi-participant secure meeting. In this manner, virtual medical examination system 20 allows for multi-physician medical examinations and real-time consultations which previously may have been cost prohibitive or otherwise infeasible.

In certain implementations, video conferencing server 42 is configured as a plurality of geographically distributed video conferencing servers that are interconnected via the internet. The use of distributed video conferencing servers allows for load balancing of the various servers to maintain optimum performance. Video conferencing server 42 can be configured to require users to provide passwords or other evidence of their authorization to participate in a video conference to better ensure that the confidentiality of patient information is not compromised. In one embodiment, videoconferencing server 42 is a session-initiation protocol ("SIP") server Other protocols for establishing video conferencing are also available. For example, video conferencing can be established using IP Multimedia Subsystem (IMS), Media Gateway Control Protocol, Real-Time Transport Protocol (RTP) or any other suitable protocol.

In one embodiment, patient device 36 and physician device 38 receive their content from a remote content manager server 44 connected to network 50. In one embodiment, when devices 36 and 38 are activated, they retrieve programs that launch graphical user interfaces from content manager server 44 via network 50. This allows for the centralized updating of the software and interfaces used by the devices 36 and 38 and avoids the necessity of individually revising the software used in devices 36 and 38. In one embodiment, network 50 is the Internet, in which case content manager server 44 may be referred to as a content manager internet server. In other embodiments, content manager server 44 supplies devices 36 and 38 with one or more programs that provide a common platform to facilitate that receipt, transmission, and display of patient data and patient/physician voice and video data. Patient device 36 and physician device 38 may take a variety of forms, such as a standard personal computer, tablet computer, smartphone, etc. In one embodiment, patient device 36 and physician device 38 include a visual display, a camera, and a speaker and patient navigation via screen-displayed icons.

In one embodiment, devices 36 and 38 are handheld computing devices such mobile phones, PDAs, smartphones, tablets, notebooks, computers, netbooks or any other suitable communication device. One suitable type of patient device 36 or physician device 38 is, for example, 10.4" Intel® Atom™ N450 Portable Medical PC. Other suitable devices of varying size and architecture are available. For example, a 17" Portable Medical PC can be used in lieu of the 10.4" Portable Medical PC. Another type of suitable device includes a TFT (thin film transistor) LCD resistive touch screen display and an integrated Bluetooth-enabled wireless transmitter. Another suitable patient device 36 or physician device 38 includes an integrated Bluetooth module, a 2.0 Megapixel CMOS camera, and a 12 Active Matix Panel resistive touch screen visual display. It also includes a bar code scanner that facilitates the reading of patient identification information from bar codes.

Figure 2:
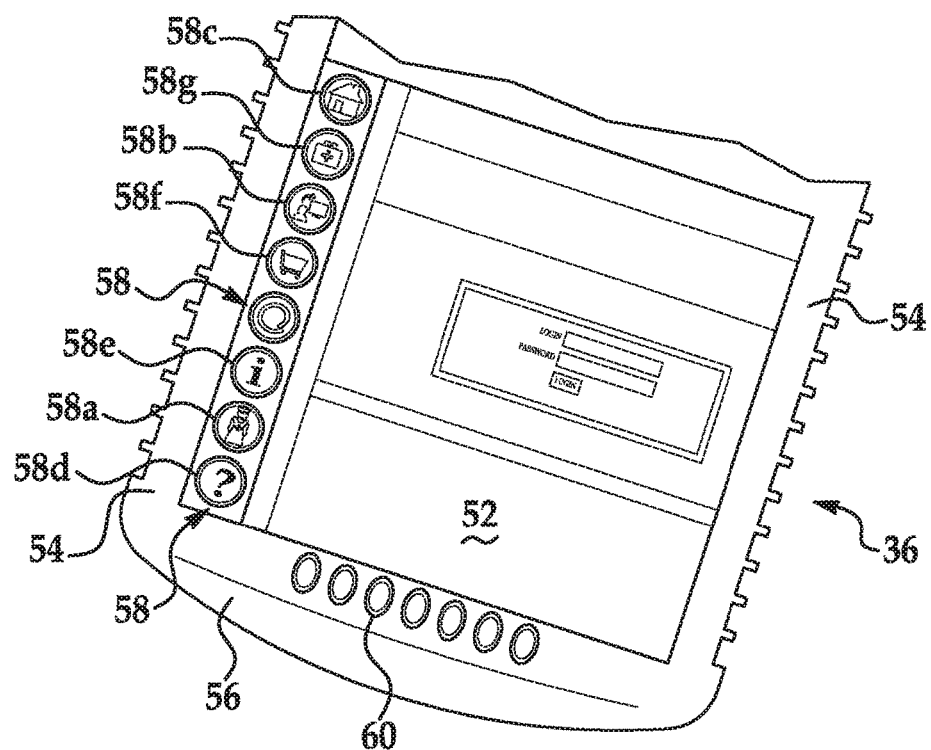
FIG. 2 is a schematic diagram of a patient device or a physician device used in the system of FIG. 1.

Referring to FIG. 2, an exemplary patient device 36 is shown, which also may also be used as a physician device 38. Patient device 36 includes a visual display 52 which can include a touch screen. Plastic side grips 54 are provided to facilitate hand gripping of device 36. Visual display 52 may include a screen with one or more icons 58 that allow the user to initiate various operations. For example, icons 58 can include a collect patient diagnostic information icon 58 *a*, an initiation of a video conference call 58 *b*, a return to home icon 58 *c*, a help icon 58 *d*, an internet icon 58 *e* (i.e. to access the Internet), a shopping cart icon 58 *f* (i.e. to purchase items and/or services) and a health record information icon 58 *g* to view current and historical patient diagnostic information. Other icons are also possible. Speaker 56 is provided to receive voice communications from a physician, and buttons 60 are provided to allow the user to initiate operations (in addition to or instead of graphical icons 58).

Figure 3:
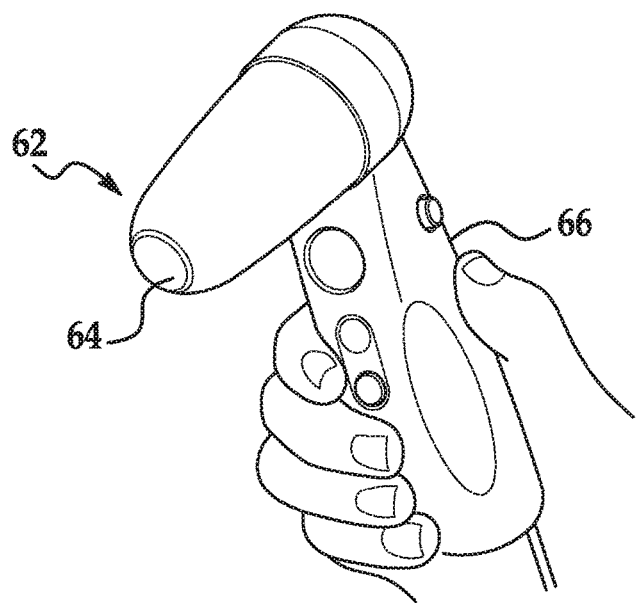
FIG. 3 is a schematic diagram of an exemplary diagnostic device for use in the system of FIG. 1.

During certain examinations, it may be desirable to transmit images of a patient's body to the treating physician. In certain cases, a camera mounted on or integrally provided with device 36 may be sufficient to generate the necessary images. In other cases, however, it may be desirable to obtain and transmit magnified images to the physician. Thus, in certain embodiments, diagnostic devices 32 include a digital microscope 62, as shown in FIG. 3. Digital microscope 62 can include a lens section 64 and a handle 66. Digital microscope 62 can also include a wireless transmitter, which is Bluetooth-enabled. Thus, in certain embodiments, digital microscope images generated by digital microscope 62 can be received and encrypted by device 36 and transmitted to videoconferencing server 42. The images can be then received from videoconferencing server 42 and decrypted by physician device 36 for display thereon. A separate recording server may also be provided to record the digital microscope images (or any other transmission from the video conference call) for subsequent storage in patient records server 40. Alternatively, the digital microscope images can be stored directly in patient records server 40. In accordance with one example, the specific patient-physician video and voice communications from a video conference may be stored with the patient's medical records in patient records server 40 for subsequent retrieval and review, thereby providing an accurate history of patient-physician communications.

As mentioned previously, patient device 36 and physician device 38 can include a graphical user interface (GUI) supplied by, for example, content manager server 44 which facilitates the initiation of desired functions. Referring to FIGS. 4A-D, exemplary GUI screen from patient device 36 and/or physician device 38 are shown.

Figure 4A:
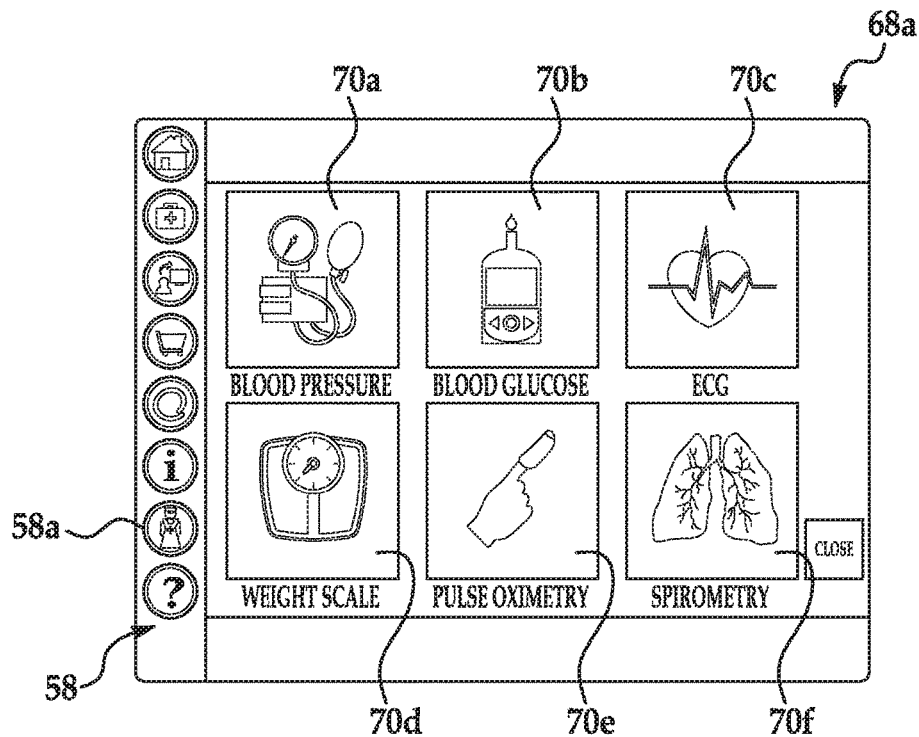
FIGS. 4A, 4B, 4C and 4D are an exemplary graphical user interface screens on the patient device of FIG. 2.

FIG. 4A is a screen 68 *a* on patient device 36 presented to a patient who has selected the collect patient diagnostic information icon 58 *a*. When collect patient diagnostic information icon 58 *a* is selected, the patient is presented with one or more selectable touch screen buttons so that patient device 36 can identify that a diagnostic procedure will be performed by the patient using diagnostic device 32. In this example, the patient is presented with the option to take their blood pressure by selecting button 70 *a*, take their blood glucose by selecting button 70 *b*, their ECG by selecting button 70 *c*, their weight by selecting button 70 *d*, their pulse/oxy by selecting button 70 *e* or their spirometer reading by selecting button 70 *f*. Each button can receive patient diagnostic information specific to the diagnostic procedure being performed. In some instances, alterative or more or less diagnostic procedures can be displayed to the patient on screen 68 *a*.

Figure 4B:
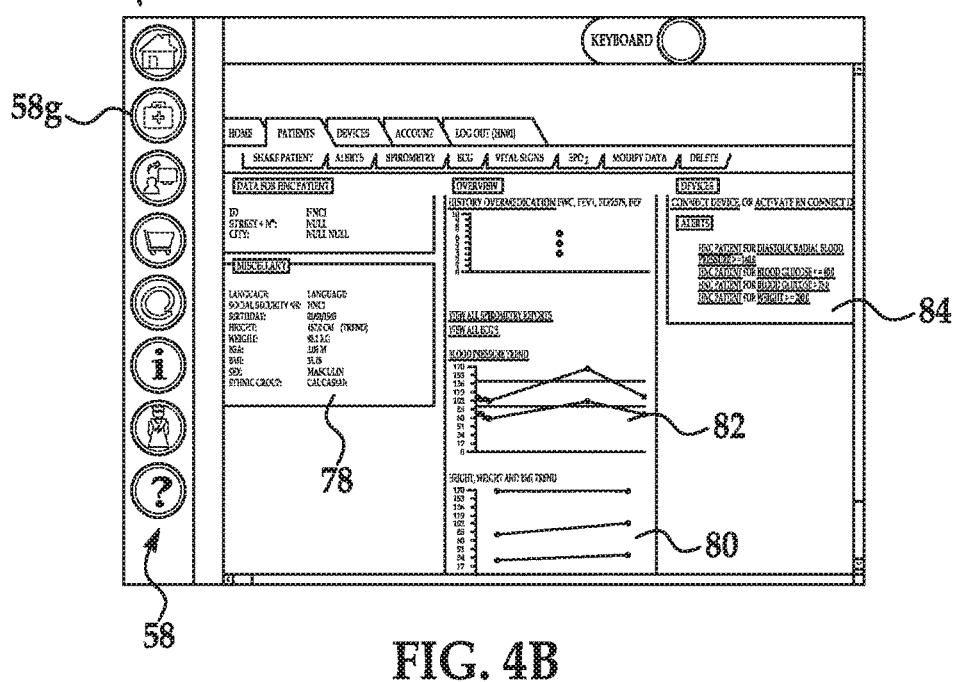

FIG. 4B is a screen 68 *b* on patient device 36 presented to a patient who has selected the health record information icon 58 *g*. When the health record information icon 58 *g* is selected the patient is able to view current or historical data related to the diagnostic procedures that have been performed using diagnostic devices 32. For example, screen 68 *b* includes patient data 78 such as name, birthday, height, weight, etc., height, weight. Screen 68 *b* also includes trend data for the patient showing developments for, for example, height, weight and bmi trend data 80 or blood pressure trend data 82. Patient can also view alerts 84 related to his/her health. For example, if the patient has abnormally high blood pressure, the alert can indicate that the patient should immediately contact a hospital. Other configurations of screen 68 *b* are also possible.

Figure 4C:
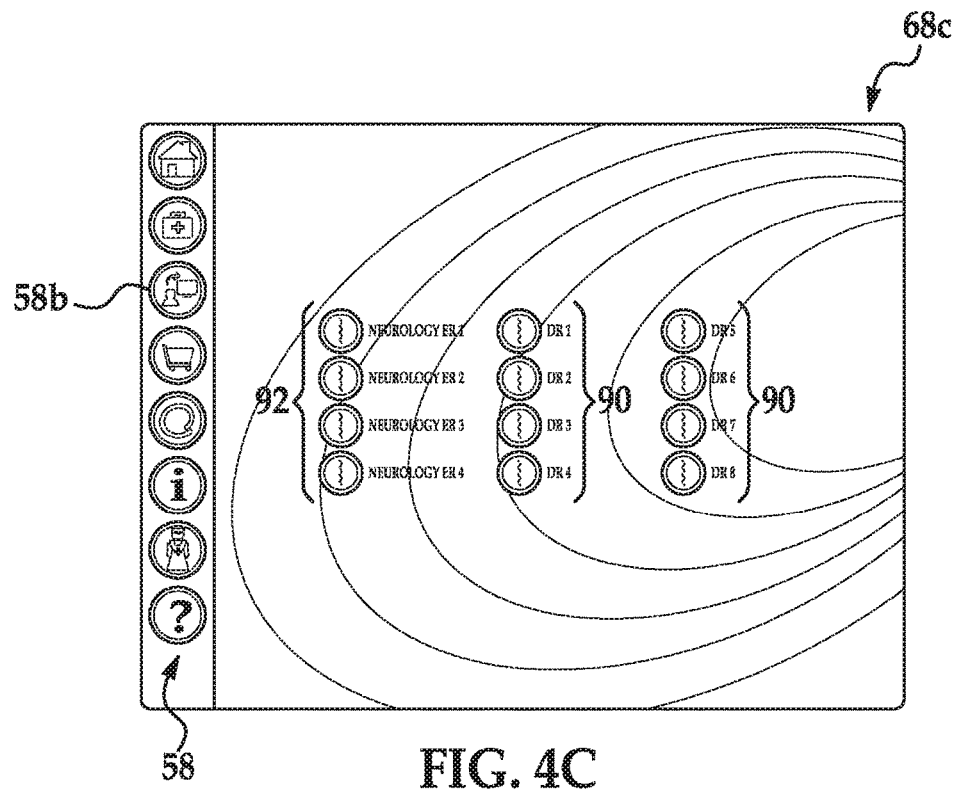

FIG. 4C is a screen 68 *c* on patient device 36 presented to a patient who has selected the initiation of a video conference call 58 *b*. In this is a graphical user interface screen that allows the user to place a video conference call with a specific doctor conference rooms by selecting one of touch screen buttons 90 or to enter one or more general conference rooms by selecting one of touch screen buttons 92. A similar screen can also be presented on physician device 36. Accordingly, the patient and/or doctor(s) can conduct a video conference if both have entered the same conference room. Communications via the patient and doctor (or between doctors), as discussed previously, is encrypted and secure.

Alternatively to having conference rooms, or in addition, screen 68 can include a key pad section, an icon section, and a speed dial section. The key pad section includes phone button images that can allow the patient to key in the telephone number of the doctor participating in the video conference call. The speed dial section can allow the user to pre-program the phone numbers of selected doctors and to associate a designated "button" with each doctor to provide one-touch dialing. The icon section can include various icons that allow a user to initiate desired operations such as calling 911, accessing a phone directory, initiating video for a video call, taking diagnostic data with a diagnostic device 32, accessing a medical supplies web site to purchase supplies, and accessing health care information.

Figure 4D:
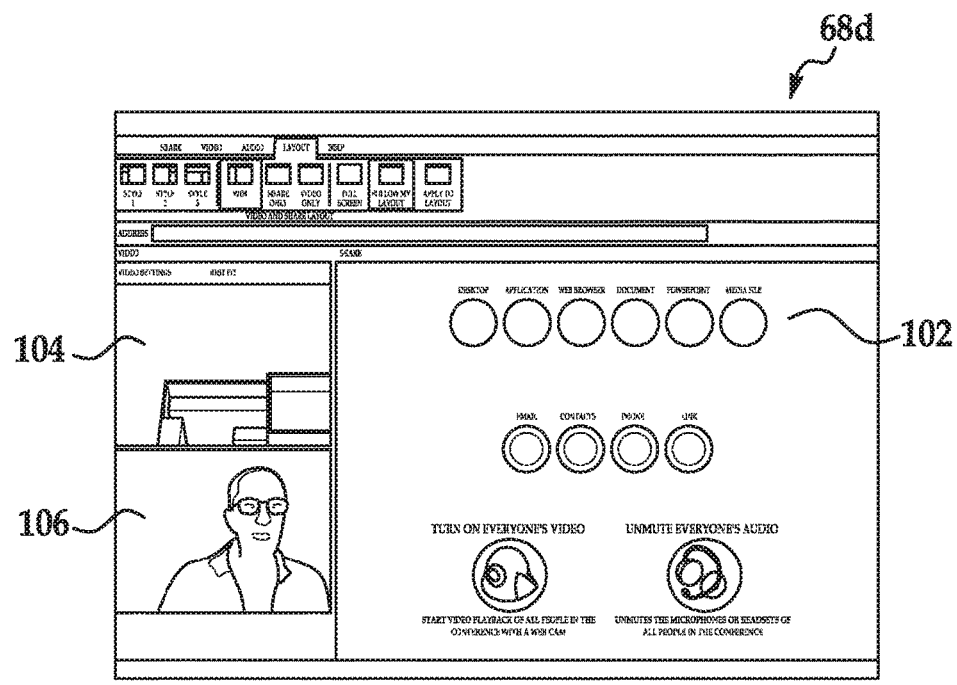

Once a video conference room has been selected, the patient (or doctor) can be presented with a screen 68 *d* illustrated in FIG. 4D showing a patient and/or physician device conducting a video conference. In accordance with the example, screen 69 includes an icon section 102, and a plurality of video display sections, such as first video display section 104 and a second video display section 106. Video display sections 104 and 106 can display video images of different video conference participants. For example, for patient device 36, video display section 104 may display the primary treating physician, and video display section 106 may display a consulting physician or specialist. In addition, video display section 104 may be used to provide the patient with a video image of himself as generated by a camera on device 36. For a physician device 38, video display section 104 may be used to display the image of the patient generated by a camera located on patient device 36 while video display section 106 may be used to display the image of the patient generated by digital microscope 62. In one embodiment, a GUI screen is provided which allows the physician and/or patient to view video images and patient diagnostic information simultaneously.

Device 36 can also have screens displaying tutorials or advertisements related to diagnostic devices 32. For example, in one embodiment, the GUI on device 36 can display tutorial information for aid in using the diagnostic device so that the patient is able to properly transmit the information to system 20. They tutorial may be interactive or non-interactive. In an interactive tutorial, the tutorial may prompt the user to indicate when they have performed a certain action. The following are exemplary prompts for blood pressure tutorial using a sphygmomanometer device and the prompts that the patient will encounter.

1. Put on cuff, left arm, with pressurizing hose at crook of elbow.

2. Press Power button on 2-in-1; cuff will inflate and slowly deflate.

3. When blood pressure reading shows on screen, press "Blood Pressure" icon.

4. Data will transfer and blood pressure device powers off and "Successful" message appears on your patient device.

The patient can verify once they have performed a one of the actions. Other tutorials are possible.

Device 36 can also be used to generate advertisements to the patient. For example, if it is determined that the patient's blood glucose level is too high, an advertisement for a blood glucose medication can be generated for display on the device's GUI. They advertisements may be run when device 36 is powered on, periodically when device 36 is running, prior to device 36 shutting down or at any other suitable time. They devices may or may not be tailored specific to the patient. The advertisements may change over time by, for example, an update from the content manager server 42. Alternatively, the advertisements can be pre-programmed into device 36 when, for example, the patient receives device 36.

Figure 5:
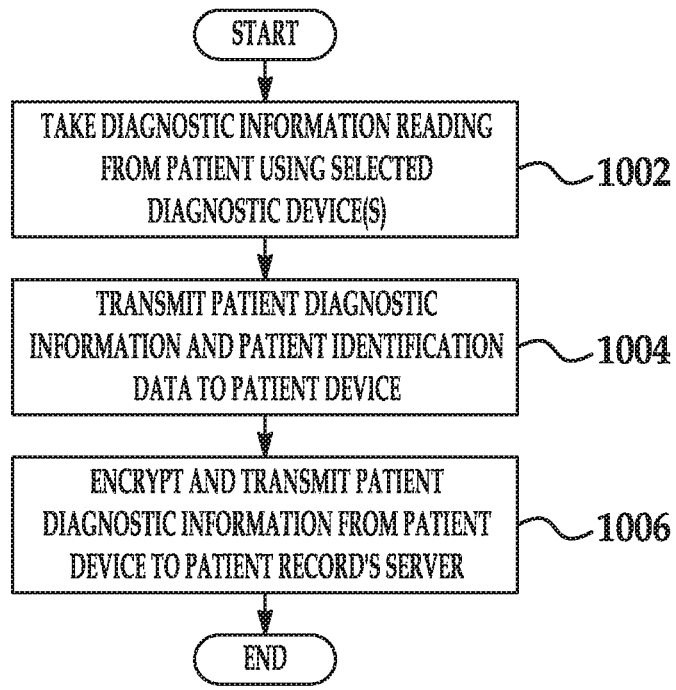
FIG. 5 is a flowchart diagram depicting an exemplary method of generating patient diagnostic information and securely transmitting and storing the data in a patient records server.

Referring to FIG. 5, a method of using virtual medical examination system 20 to generate and securely transmit patient diagnostic information to patient records server 40 will now be described. In accordance with the method, a patient selects one or more diagnostic devices 32 of the type described previously. In step 1002, the patient uses the diagnostic device 32 to generate diagnostic data (e.g., blood pressure, blood chemistry, pulse oximetry, weight, spirometry, etc.). Diagnostic device 32 transmits (wirelessly or via a wired connection) patient diagnostic information to patient device 36.

In step 1004, patient device 36 encrypts patient diagnostic information and information identifying the patient (hereinafter patient identification data) using an encryption protocol such as https. Patient device 36 then transmits the encrypted data to patient record server 44 via network 50, which can be the internet or any other communication network. Patient record server 40 can have a unique network address (e.g., IP address), that allows the patient device 36 to uniquely identify it as the intended recipient of the encrypted patient diagnostic information and patient identification data. The patient record server 40 stores the patient diagnostic information in association with the patient identification data so that the data is accurately identified with the correct patient when retrieved by a health care provider. When the connection between patient device 36 and diagnostic device 32 is wireless, patient can beneficially perform diagnostic tests without having to make a wired connection to the diagnostic device 32 and a computer or other transmitting device. Instead, the patient need only activate the diagnostic device 32 and locate it within the zone of transmission of the patient device 32.

In certain examples, diagnostic devices 32 are pre-configured to generate wireless signals comprising patient identification data that corresponds to a specific patient to which diagnostic devices 32 have been uniquely assigned. For example, each patient may be assigned a unique numeric or alphanumeric code, which corresponds to a particular wireless signal generated by diagnostic devices 32. In one example, the patient files resident in patient record server 40 are setup via the web. When subsequent diagnostics are taken they are applied to the file by opening the utility ready for the diagnostic information to be captured.

Figure 6:
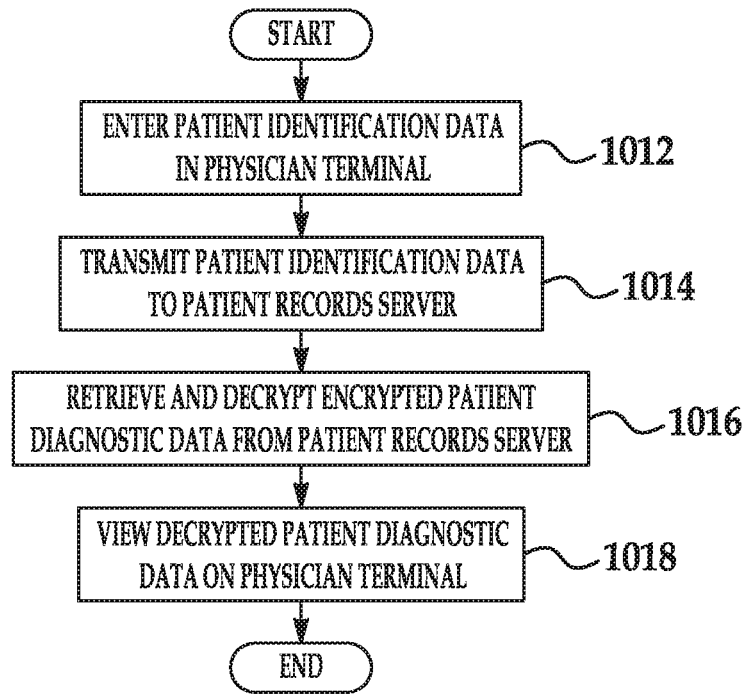
FIG. 6 is a flowchart diagram depicting an exemplary method of securely retrieving patient diagnostic information from a patient records server and displaying the retrieved data on a physician device.

Referring to FIG. 6, a method of securely retrieving patient diagnostic information from patient record server 40 is described. In accordance with the method, a physician can enter patient identification information into physician device 38 such as by using touch screen 52) at step 1012. Next, at step 1012, physician device 38 can transmit (via a wired or wireless connection) the patient identification information to patient record server 40 via network 50. Patient record server 40 can cause a graphical user interface to be displayed on physician device 38 which requests certain physician credential information (e.g., a log-in name and a password). Patient record server 40 may be physically resident at a facility such a hospital or clinic with which the physician is associated, although the physician may be remotely located from server 40 when accessing it. Alternatively, the physician may sign into patient record server 40 before transmitting patient identification data to it.

Once the physician's authorization to review data for a specific patient is confirmed, the data is transmitted in encrypted form to physician device 38. At step 1016, physician device 38 can include executable code (which may be provided by content manager server 44) to allow for the decrypting of encrypted patient diagnostic information. The patient diagnostic information can then be display on physician device 38 to be viewed by the physician at step 1018.

Figure 7:
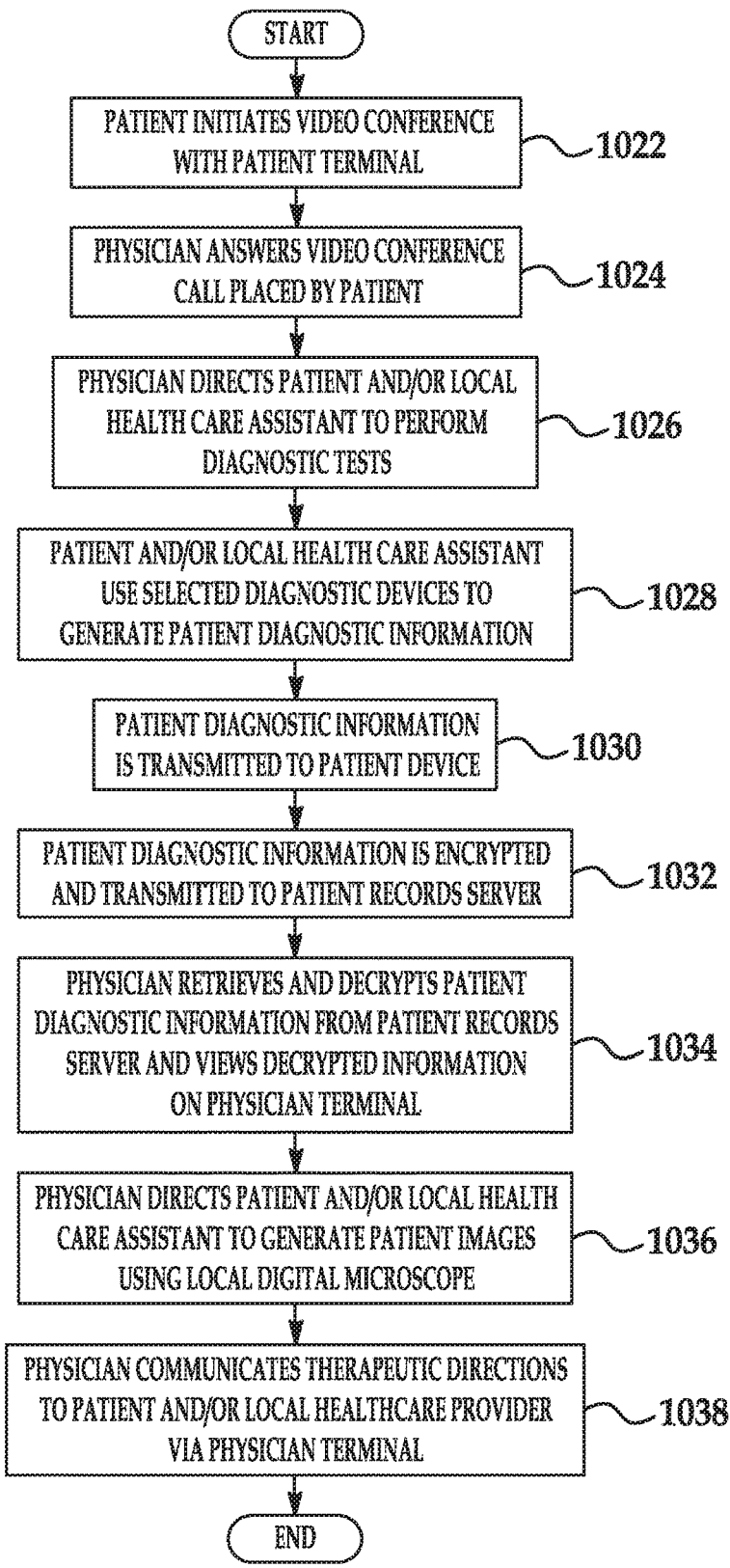
FIG. 7 is a flowchart depicting an exemplary method of performing a virtual medical examination.

Referring to FIG. 7, an exemplary method of performing a virtual medical examination of a remotely located patient is described In step 1022, the patient initiates a video conference call using patient device 36 as described previously. A conference call is then initiated with videoconferencing server 42. Videoconferencing server 42 transmits data to physician device 38 indicating that a call has been initiated. The patient may then use an icon in icon section 58 to activate a camera on patient device 36 and begin the transmission of encrypted patient video data to videoconferencing server 42.

In step 1024, the physician answers the patient's call by pressing appropriate virtual or physical keys on physician device 38. In certain examples, the patient receives video images from a camera on the physician device 38 in video display section 76 and sees the video data generated by a camera on patient device 36 in video display section 77. Correspondingly, the physician may see video images generated by the camera on patient device 36 in video display section 76 of physician device 38 and video images of herself in video display section 77.

In certain examples, the patient may be at his or her home during the virtual medical examination. In other examples, the patient may be alone during the examination. In additional examples, the patient may be with another individual who can assist in the performance of the examination. In one scenario, the patient is in a clinic or hospital and is assisted by a local health care assistant (e.g., nurse or doctor) in providing the remote physician with the diagnostic data necessary to develop a treatment plan. After taking a verbal medical history from the patient and inquiring about any medical issues that may have prompted the request for an examination, the physician can, for example, provide health instruction information to the patient or local health care assistant. For example, the physician can direct the patient and/or a local health care assistant to perform diagnostic tests on the patient using selected diagnostic devices 32 (step 1026). For example, the physician may direct a local health care assistant to take blood pressure readings or measure the patients weight. The patient and/or local health care assistant can then use one or more diagnostic devices to generate the patient diagnostic information at step 1028.

As used herein, health instruction information includes any information received from the physician or other health care provider Health instruction information can be generated from physician device 38 and transmitted to patient device 36 in real-time so that the patient or other health care provider can, administer medication, perform a diagnostic procedure, taking vital signs, manipulate a digital microscope (e.g. digital microscope 62 to a certain region of the patient's body or any other action. In some instances, health instruction information may not necessitate any immediate action by the patient. For example, the physician may indicate through health instruction information that the patient should take their temperature in one hour. However, the health instruction information is transmitted and received by the patient in real-time.

Health instruction information can be in the form of voice, text or image data or any other suitable type of data. For example, when voice data is the form in which health instruction information is formulated, the voice data can be transmitted to video conferencing server 42. Voice data can be oral instructions to the patient. When text or image data is the form in which health instruction information, the text or image data can be transmitted to the patient records server 40. For example, the physician can send a message to a patient to "take blood pressure" rather than communicating the instruction orally. Other suitable techniques for transmitting health instruction information are possible. For example, image data can be sent to video conferencing server 42 rather than patient records server 40.

As discussed previously, transmitters in the diagnostic devices 32 can wirelessly transmit patient diagnostic information generated by diagnostic devices 32 to patient device 36 in association with patient identification information, for example, a unique alphanumeric code assigned to the patient (step 1030). The wireless transmission of diagnostic data to patient device 36 can be performed using the Bluetooth protocol. The patient device 36 can encrypt the received patient diagnostic information and patient identification data, using an https protocol or any other secure protocol. Thus encrypted, the patient identification data and patient diagnostic information can be transmitted to the patient record server 40 (step 1032). Using physician device 38, the physician can access patient record server 40 upon login using permissions-assigned passwords for safety and confidentiality and can retrieve and decrypt the patient diagnostic information which is then displayed on physician device 38 (step 1034) In certain examples, the patient diagnostic information is also transmitted to the patient device 36, where it is decrypted and displayed to the patient. The concurrent transmission of patient diagnostic information from patient device 36 to physician device 38 while the patient device 36 and physician device 38 exchange information to conduct a secure video conference session are in real-time.

In certain situations, the physician may wish to obtain microscope images of certain areas of the patient's body In such situations, the physician may direct the patient and/or a local health care assistant (such as an emergency room doctor, a nurse, or a physician's assistant) to manipulate digital microscope 62 (or other diagnostic device 32) to selected regions of the patient's body to obtain the desired microscope images (step 1036). Digital microscope 62 can transmit video data of the images to patient device 36 which then encrypts and transmits the video data to video conference server 42 for subsequent retrieval by the physician and viewing on the physician device 38. At the outset of the call or during the call, the treating physician may ask another health care provider, such as a specialist, to join the video conference. The specialist can access the videoconference server (such as by inputting an IP address or domain name for the videoconference server into his or her computer terminal). After supplying the appropriate authorization credentials (such as a log in and password), the specialist will be connected to the call.

In step 1038, the physician (alone or in conjunction with a consultant or specialist) communicates therapeutic directions to the patient using physician device 38. Alternatively, the physician may consider the information provided during the video conference and may conduct a subsequent video conference to provide therapeutic directions. In another scenario, the physician may conduct a secure video conference with another physician and both physicians may view patient diagnostic information from the patient records server 40 to collaborate and develop a joint treatment plan. The method of FIG. 8 may be used for the diagnosis and treatment of recurring or non-recurring conditions, and it may also be used to perform periodic monitoring of patients with chronic conditions, such as diabetes. The method of FIG. 7 is not limited to the treatment of any one particular condition, and exemplary conditions include diabetes, asthma, hypertension, chronic obstructive pulmonary disease, and heart failure or any other condition.

Exemplary Application

The following is an exemplary application for transmitting patient diagnostic information to a remotely located physician who is using a handheld device such as a mobile phone (e.g. physician device 38). A diagnostic device (e.g., diagnostic device 32), which is Bluetooth-enabled, can wirelessly transmit patient diagnostic information to a patient device (e.g., patient device 36), which is also Bluetooth enabled. The patient device can encrypt and transmit the patient diagnostic information to a patient information sever such as a patient records server 40. The patient information server records the received patient diagnostic information in a patient file and then re-transmits the data to the patient device and a physician device. Access to the patient diagnostic information can be controlled via a set of administrator permissions and all patient data can be shelled within a secure HIPAA compliant environment to ensure confidentiality of data via, for example, encrypted HTTPS communication.

A secure videoconference can be conducted between one or more physicians and a patient in a virtual conference room so that the patient and the physician can access the diagnostic information in real-time during the videoconferencing session After reviewing patient diagnostic information, a physician, via his physician device, can initiate a videoconference with the patient and/or one or more additional physicians (or other healthcare providers). Each physician can access have access to the diagnostic information and be part of the videoconferencing session via their handheld device. As such, each physician can receive the diagnostic information real-time regardless of their location and review the diagnostic information to provide health instruction information. For example, a physician joining the video conference such as a specialist may request that that a certain diagnostic procedure be performed on the patient that was not requested by the physician who was initially part of the video conference. A recording server (e.g. patient records server 40) can record all voice and video data from the conference. The virtual conference rooms can be provided by a videoconferencing server (e.g., video conferencing server 42) that can provide, for example, secure https encryption of all voice and video data.

Alternatively, as discussed previously, the embodiments of remote patient device 36, physician device 38, patient records server 40, videoconferencing server 42 and/or remote content manager server 44 (and the algorithms, methods, instructions etc. stored thereon and/or executed thereby) can be implemented in hardware, software, or any combination thereof including, for example, IP cores, ASICS, programmable logic arrays, quantum or molecular processors, optical processors, programmable logic controllers, microcode, firmware, microcontrollers, servers, microprocessors, digital signal processors or any other suitable circuit In the claims, the term "processor" should be understood as encompassing any the foregoing devices, either singly or in combination. The terms "signal" and "data" are used interchangeably. Further, portions of remote patient device 36, physician device 38, patient records server 40, videoconferencing server 42 and/or remote content manager server 44 do not necessarily have to be implemented in the same manner.

Further, in one embodiment, for example, remote patient device 36, physician device 38, patient records server 40, videoconferencing server 42 or remote content manager server 44 can be implemented using a general purpose computer/processor with a computer program that, when executed, carries out any of the respective methods, algorithms and/or instructions described herein In addition or alternatively, for example, a special purpose computer/processor can be utilized which can contain specialized hardware for carrying out any of the methods, algorithms, or instructions described herein Other embodiments of the present apparatus and methods may optionally in any combination include additional features such as: configured for manual or automatic entry and storage of patient diagnostic data in a HIPAA compliant encrypted environment; single patient data is selectable for review; single patient data may be mergable with multiple patient's data into charts, graphs, reports for examination of patient populations; patient data, video and audio may be connectable and transmittable simultaneously by one of satellite, cellular, LAN, or WIFi in a HIPAA compliant encrypted environment; views, transfers and stored images, videos and audio are in a HIPAA compliant encrypted environment; push content to patients, including one of educational videos, health news, health alerts, or prescriptions in a HIPAA compliant encrypted environment; generated remote prescriptions for delivery to patient in a HIP AA compliant encrypted environment; perform every patient data claim can also be performed without video utilizing a gateway connection; perform every patient data claim without a computer utilizing a specialized gateway connection; auto-schedule patient appointments within a virtual clinic; place patients in a virtual waiting room prior to a virtual exam, and simultaneously connect multiple participants in an examination irrespective of their geographic location in a HIPAA compliant encrypted environment.

The gateway can work as data receiver and transmitter, which helps users or their healthcare providers to manage data easily and remotely. With the gateway, healthcare providers can monitor and analyze test results remotely and effectively through the connection to the server. Data results can be viewed in various formats (HTTP, XML, TCP/IP-, etc.). The gateway is intended to transmit selected medical information (i.e. blood glucose, blood pressure, Sp02, body weight, BMI, temperature, and the like) measured by compatible devices via Bluetooth or other wireless devices and transmitted over encrypted network using WAN/LAN or 4G Carrier and the like and combinations thereof.

According to another approach, the present embodiment may also be applied in an ICU setting as part of an e-ICU Monitoring System. Advances in communications, video displays, monitoring devices and computers have made it possible to remotely monitor hundreds of monitored patients. In this instance, a medical information system receives patient data and information from various sources such as described herein as well as inherent to an ICU and displays from ICU monitoring system. This system allows combination of a real-time, multi-node telemedicine network and an integrated, patient care management system to enable specially-trained Intensivists to provide 24-hour/7-day-per-week patient monitoring and management to multiple, geographically dispersed ICUs from both on-site and remote locations.

A member of the medical team can record observations about a patient using key words and phrases which can be supplemented with additional text for customized notation. Multiple types of patient data can be selectively displayed simultaneously, and to multiple remote users. The system can access stored data according to user-specified formulae to compute a score or metric which reflects a relationship between various factors, each factor being weighted appropriately according to its significance as defined in the formula.

This e-ICU system allows a medical information system which displays all types of medical information about a patient in a variety of easily understood formats in real-time. The medical devices including Ventilator, infusion pump, ECG, Blood Pressure, Blood Glucose, Thermometer. Weight Scale, Pulse, Spirometer, and the like and transmits the information to the interface using Wireless/Bluetooth technology. The data is displayed in readable format to the monitoring screen in real-time. Alerts can be generated by the application based on parameters for each individual patient and send to assigned team member either as text or email. Each screen can display data for multiple patients at a time.

Figure 9:
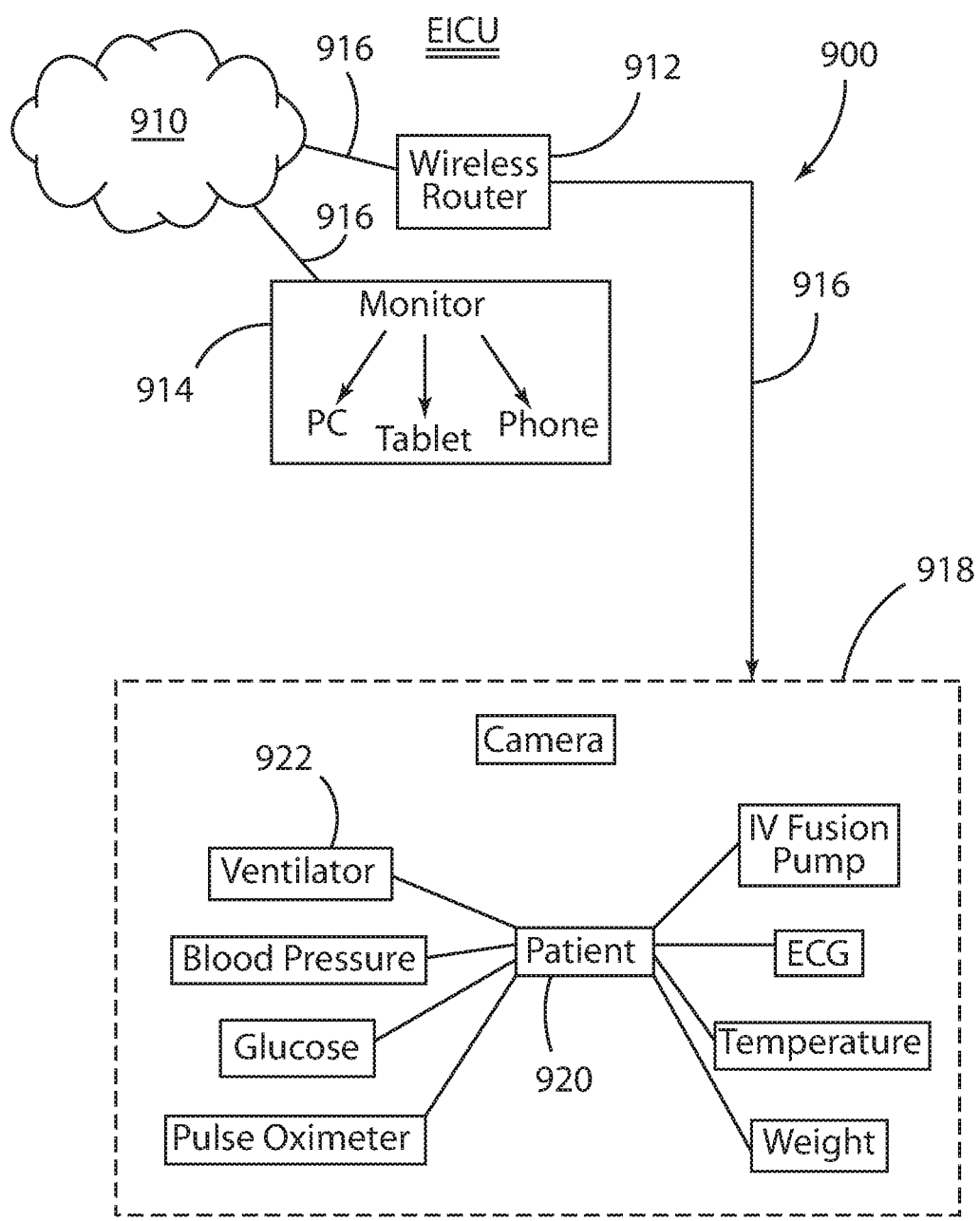
FIG. 9 illustrates an exemplary system for use in implementing methods, techniques, devices, apparatuses, systems, servers, sources and the like, in accordance with another approach of the present embodiments.

FIG. 9 illustrates data flow according to one approach of the present embodiments for an e-ICU system and is generally indicated at 900. In this approach, cloud 910, as described herein, is communicatively connected via connections 916 with a monitor 914 (such as a personal computer, a tablet computer, a smartphone and the like and combinations thereof) accessible to a health care provider. In an ICU 918 setting, a patient's 920 peripheral devices (such as a camera, ventilator, blood pressure monitor, glucose monitor, pulse oximeter, IV infusion pump, ECG, thermometer, weight scale, and the like and combinations thereof) can also be communicately connected to cloud 910 via a wireless router 912.

In another approach, the present embodiments can begin with a patient logging into the system. When system has reviewed the users enter credentials, either by manually entered password, voice activation, facial recognition, thumbprint and the like, the patient may select from a variety of menus. For example, the patient may select the "Clinician" menu from the screen. The patient can then select from a variety of options, such as "Take Your Vitals Now". In this screen, the user may then select from a variety of peripheral devices as described herein to activate. The Patient would then touch the corresponding icon for the test. The devices can use wireless technology to communicate with the system. Patients can use the system to take various prearranged surveys. Surveys can be set be pushed daily, weekly, monthly, etc.

On the clinician's side, a clinician has the option to purchase dedicated hardware or can access the "Provider Portal" from any device with Internet connectivity. After going to the "Provider Portal" the clinician will also be asked to enter a set of credentials. At some point, such as after entering the credentials the user also may be asked to choose a language.

Credentials have varying levels to authenticate what clinician are allowed to view. The system administrator can create and assign roles. A clinician can then be taken to their patient list. On this screen, the colors may be used to represent alert/parameters set by the clinician. For example, an Alerts/Parameters tab may be set be a clinician to set vital thresholds which generate the colors on patient page. For example, green can be used to indicate that the patient is good for the day. Yellow can mean that the patient is slightly falling outside of parameters. Red can mean that the patient has fallen outside of parameters. And, black can mean that the patient has not uploaded any vitals for that day. Also, on this screen the clinician may have the ability to add notes to each patient. Each note is date and time stamped.

When clicking on a patient's ID, the clinician can be taken to that patients dashboard. The most recent uploads for that patient are displayed here. By clicking on an overview tab, an overview of all test in graph form of the past, for example, 10 results. The system and apparatus can also sort by date using filters, which can be shown on a graph. By clicking on the graph of each test, the system can drill down to each data upload that is date and time stamped. Further, vital reports from all patients can be exported by the system to electronic spread sheets. The list of the devices that are deployed to each patient can also be tracked and can also be exported to spread sheets. A share info tab may also be provided for additional doctors or specialist. The clinician, the patient, a specialist or additional professional may be allowed to view.

One approach to the present embodiments can include a medicine compliance feature. This feature delivers personalized medication reminder notifications-specific to each patient and medication. These notifications can be modified in real-time through algorithms combined with predictive analytics to constantly alter the message based on each patient's interaction with application. The result is to continually reinforce medication adherence with fresh relevant communication.

The medicine compliance feature may provide a menu of standard and custom reports which include medication usage, adherence, effectiveness, geo location, population management and the like. It is unique combination of data algorithms and analytics working with the system to help identify medication consumption problems as they happen in real time. Patients can record medication doses and caretakers are able to receive alerts via incoming, automated calls when patients appeared to have missed a dose.

In use, the medicine compliance feature will allow a patient to see their daily medication schedule and information on any smart device like phone, smart watch, web etc. about whether they taken a required dose They will also be able to access medication instructions. Each medication reminder notification includes customizable pill images, dose and schedule information. On screen, a patient may have different options to select from, for example Take the medication—(This can send notification to caretaker that the patient has taken the medicine)
Read the medication info—(This option can allow the patient to read the medication information)
Skip the medication—(This option can allow a user to skip the medication, and also notify to caretaker)
Snooze the alarm—(This can set the alarm for the next 10-15 mins, for example, for a reminder)
Dismiss the reminder—(Once it is dismissed, it can provide the information for next schedule)

For example, the medicine compliance the Application can let patient know what time to take their next scheduled dose and if the patient is scheduled to take a dose within next hour or less, he/she will receive message 'Next dose in 30 mins' etc. If the time for the last scheduled dose of the day has passed, the application is updated to show whether the final dose was 'Taken', 'Missed' or 'Skipped'.

Figure 8:
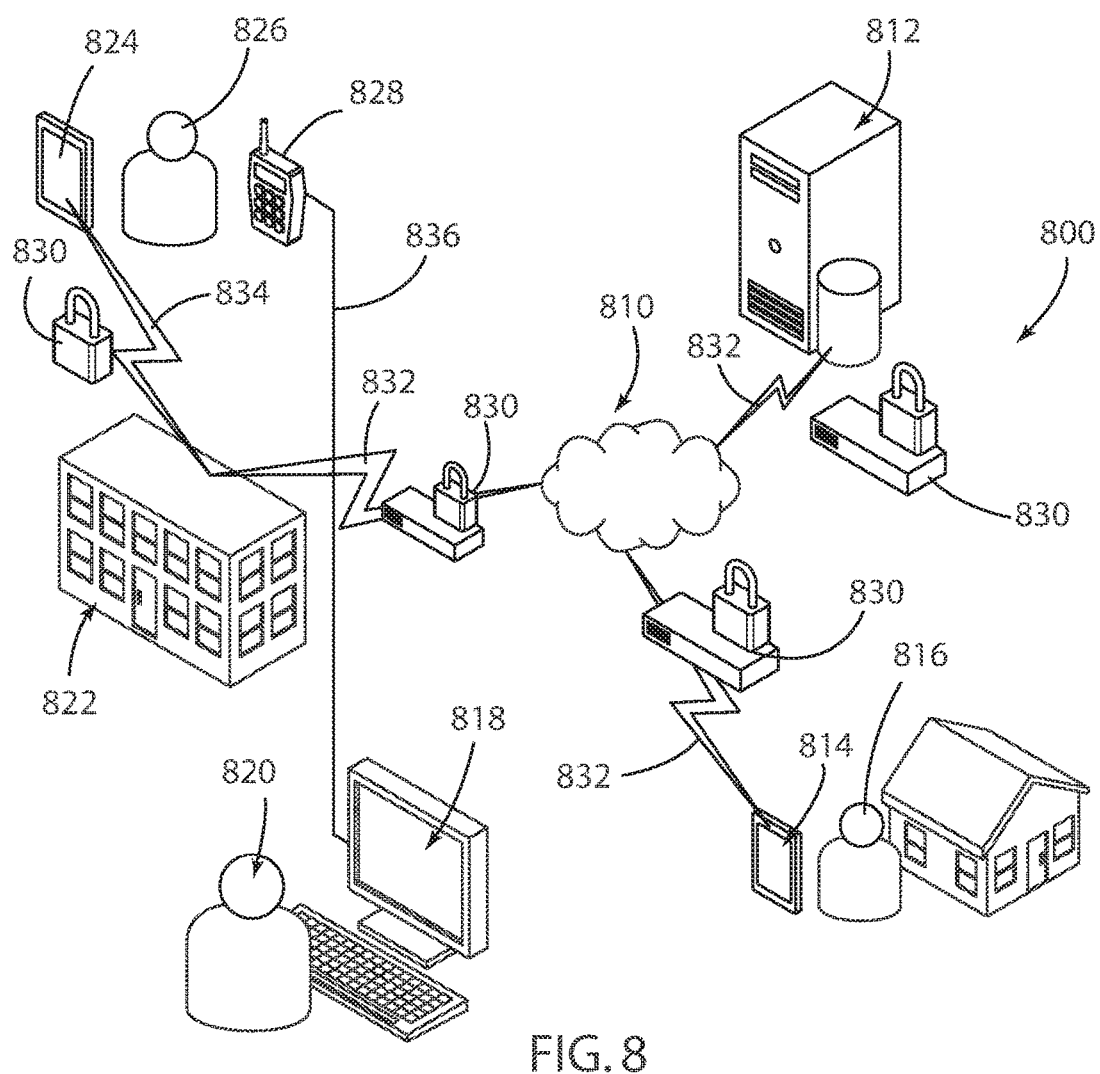
FIG. 8 illustrates an exemplary system for use in implementing methods, techniques, devices, apparatuses, systems, servers, sources and the like, in accordance with some of the present embodiments.

FIG. 8 illustrates data flow according to one approach of the present embodiments and is generally indicated at 800. A private cloud 810 is shown as connectivity point of the components of embodiment 800. Cloud computing is a type of Internet based computing. Services, data storage and computer applications can be delivered to a computing device through the Internet. Cloud computing relies on sharing computer resources rather than having local servers or personal devices handle applications. System 800, as illustrated, shows the private cloud 810 connects to an offsite backup 812, a patient 816 interface device such as a tablet 814, a medical specialist 820 interface device such as a terminal 818, and a medical care facility, such as a hospital 822. The connectivity of the system components by connections 832 are detailed herein, but also include encryption devices 830. As shown in FIG. 8, a doctor/physician 826 can be connected to the system at multiple access points such as interfaces shown of a tablet 824 or smartphone 828 and the like via connects 834 and 836. It is noted that in preferred embodiments, when doctor 826 signs on to portal (cloud) transmitted data is going though https/ssl encryption, but then also has to pass through a second layer of encryption to get in to the portal and then to the cloud.

Figure 10:
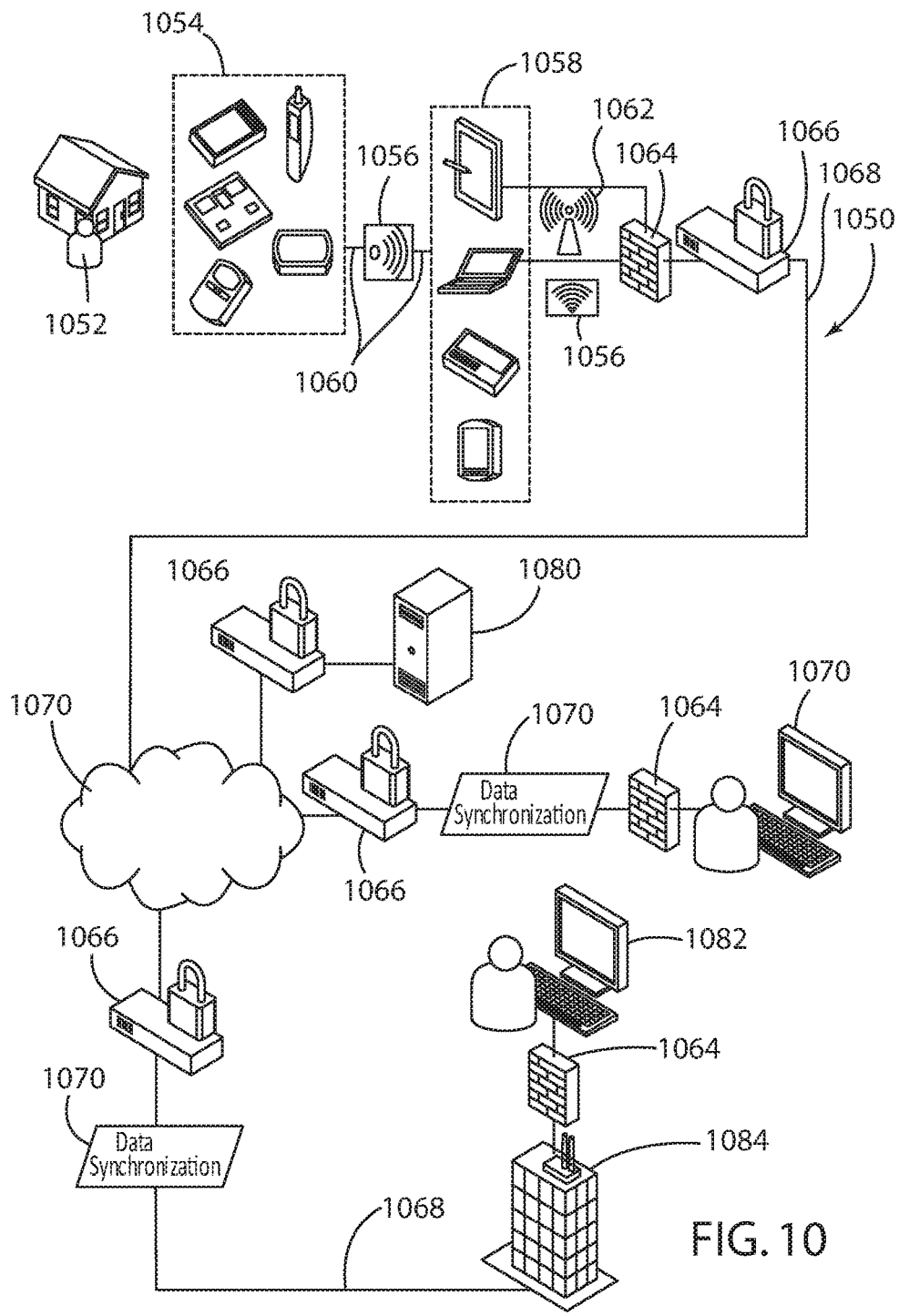
FIG. 10 illustrates an exemplary system for use in implementing methods, techniques, devices, apparatuses, systems, servers, sources and the like, in accordance with another approach of the present embodiments.

FIG. 10 illustrates data flow according to another approach of the present embodiments and is generally indicated at 1050. In this embodiment, the private cloud 1070 is communicatively connected to components of the system via connections 1068 having HTTPS/SSL connections 1064 and encryption devices 1066 (such as a device sold under the tradename SONICWALL). Data synchronization applications 1070 can be in the data stream. In this embodiment, patient 1052 interacts with various peripheral devices 1054 as described herein, which can have connections 1060 via a wireless device, such as one sold under the tradename BLUETOOTH 1056 to connect with a device 1058, which is then connected the private cloud 1070 via BLUETOOTH 1056 or cellular device 1062 connections. Devices 1058 can include a personal computer, a tablet computer, a gateway device, smart phone, and the like and combinations thereof. It is noted that a gateway device is preferably used when video capabilities are not provided. FIG. 10 also provides an off-site backup 1080, a terminal 1070 for access by a case manager, and a terminal access for a health care provider 1082 via a hospital EMR 1084 system.

Figure 11:
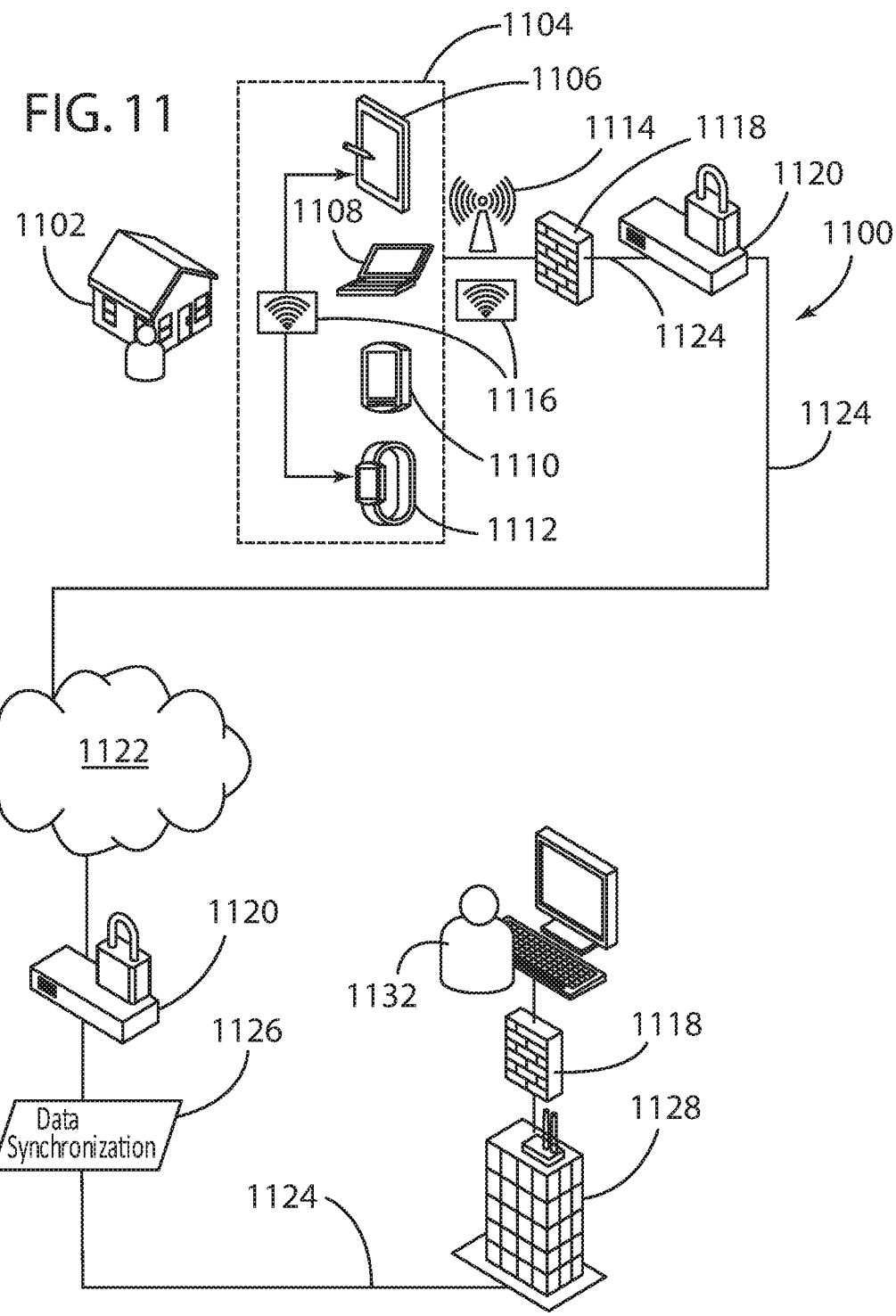
FIG. 11 illustrates an exemplary system for use in implementing methods, techniques, devices, apparatuses, systems, servers, sources and the like, in accordance with another approach of the present embodiments.

FIG. 11 illustrates data flow according to another approach of the present embodiments and is generally indicated at 1100 for patient medical compliance applications. In this embodiment, the private cloud 1122 is communicatively connected to components of the system via connections 1124 having HTTPS/SSL connections 1118 and encryption devices 1120 (such as a device sold under the tradename SONICWALL). Data synchronization applications 1126 can be in the data stream. As shown in this embodiment, a physician at terminal 1132 can set a dosage for a medication through the cloud 1122. The private cloud then can send a push notification to alert a patient 1102 when to take the medication. The push notification can be received by a patient peripheral device 1104, such as a tablet computer 1106, a personal computer 1108, a smart phone 1110, a smart watch 1112, and the like and combinations thereof. It is noted that in the preferred embodiments the smart watch 1112 is communicatively connected to a peripheral device using a BLUETOOTH or equivalent type of wireless connection 1116. The peripheral device connected to the private cloud 1122 is connected preferably via a cellular connection 1104.

Figure 13:
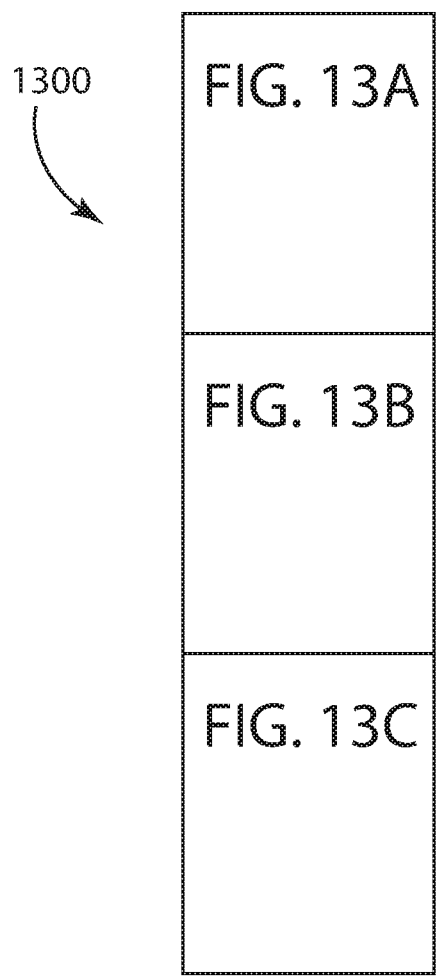
FIGS. 13A, 13B and 13C are a flowchart depicting an exemplary system and method for a patient to access a consult and a second opinion consult.
Figure 13A:
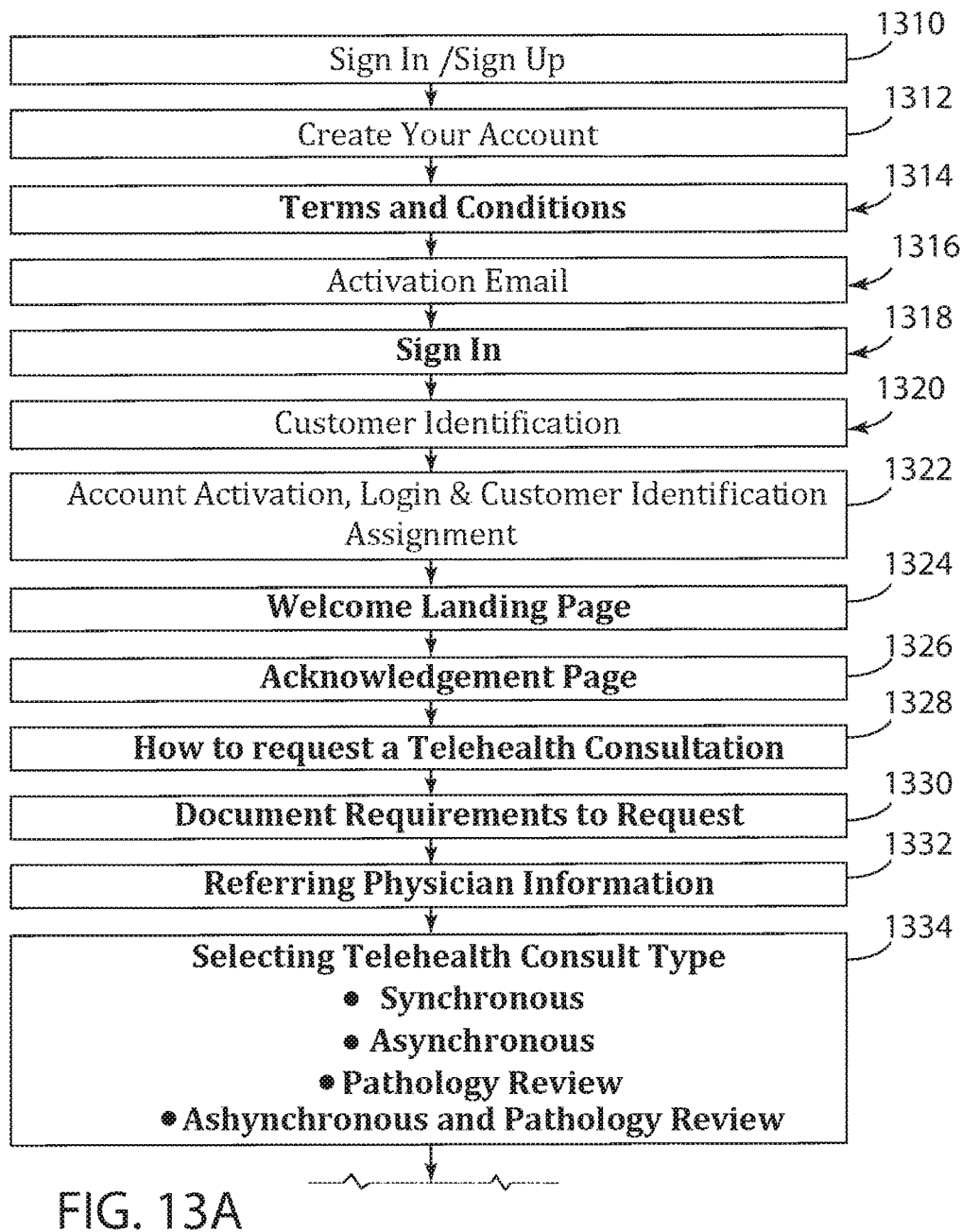
Figure 13B:
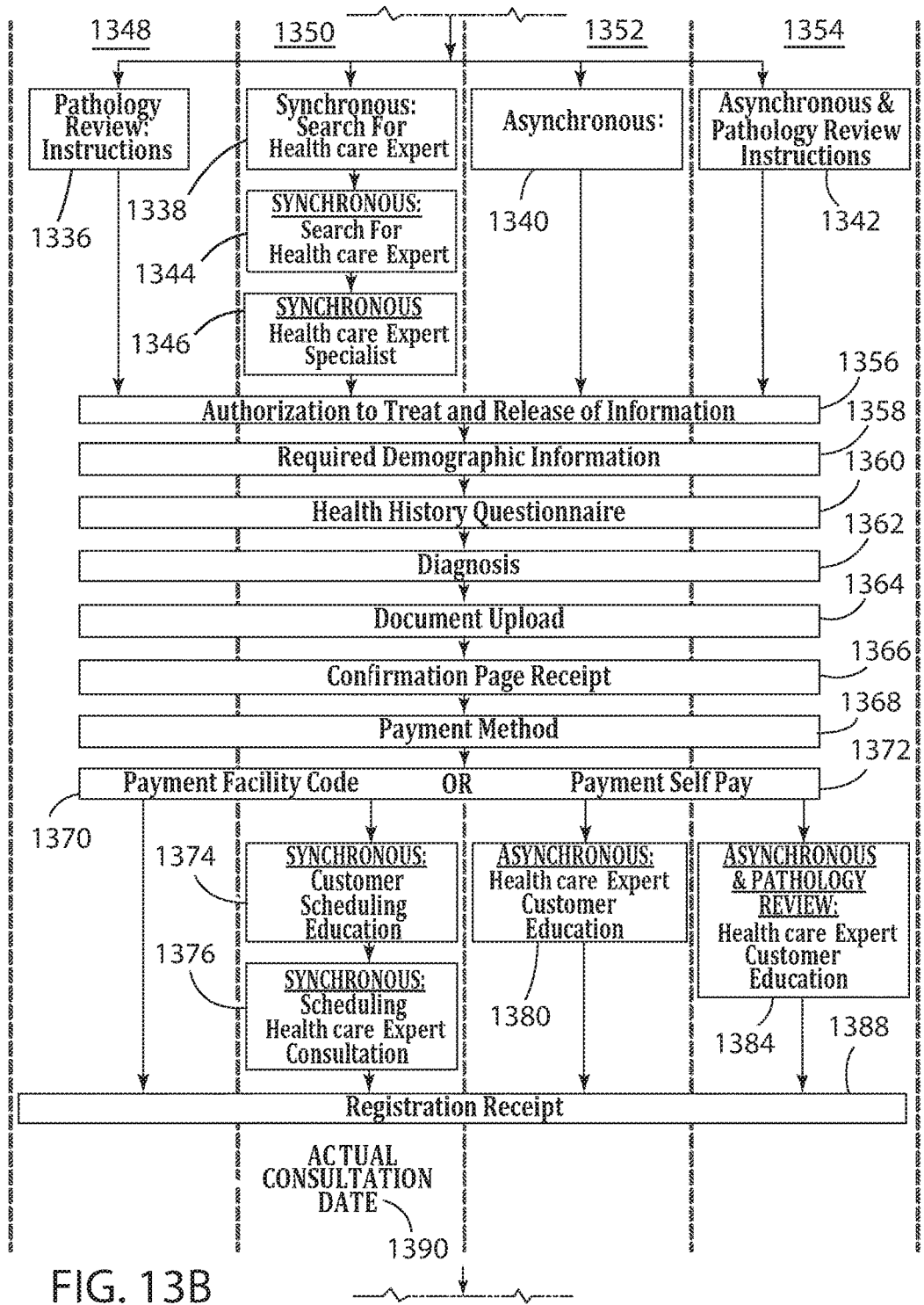

FIG. 13 illustrates data flow according to one approach of the present embodiments and is generally indicated at 1300 as a Second Opinion Platform Specifically, FIGS. 13A, 13B and 13B combine to show a flowchart depicting an exemplary system, method and device for a patient to access a consult and a second opinion consult. These embodiments, can provide international medical consultations and evaluations remotely and via a web-based platform.

Generally, in this approach, alongside a clinician, the patient may register for an account by entering preliminary information and accepting terms and conditions on the Second Opinion Platform 1300, and then receive a confirmation email from the platform to activate their account. Once the patient is logged in, the system can advance through a series of steps to build a patient profile to output a customer identification number, and for requesting, for example, a United States-based second opinion.

Thus, the system is capable of providing virtual care throughout the world. Select providers can then deliver second opinions to patients virtually. The patient and referring physician register the patient in the Second Opinion Platform, to perform documented HIPAA complaint virtual consultations and reports. According to one approach, telemedicine carts with the present systems and methods may be implemented at health care facilities. These telemedicine carts are designed to create a direct connection to a medical professional's computing system, such as a tablet computer, and to connect with them from the patient's home.

By way of example, in one medical emergency, a physician may have a four hour time period to administer the correct medication to a stroke patient, and all that is needed is a visual assessment to do so. Prior to implementing this type of stroke program, the health care facility would need to send out a patient transport, such as an ambulance or helicopter, to bring stroke patients to the hospital for the specialist to provide a visual assessment. This is time consuming and very expensive. Utilizing the present system, health care providers are able to assess a stroke patient in real-time virtually. The telemedicine cart can also now perform these services remotely and are able connect and communicate via synchronous video conferencing and control the telemedicine cart remotely by, for example, panning, tilting, and zooming the camera to focus in on the patient at the required level. The result of the present system provides greater access to specialists for their patients in a quicker timeframe while reducing travel and dollars spent.

Second Opinion Platform 1300 may have steps such as: assisting the patient in their understanding and acknowledging the service; providing education on how to request the second opinion and the time it takes to complete; receiving referring physician information if there is a referring physician; and providing choices so that a patient has the ability to choose which type of consultation they desire or need. Next, the system determines, based on the provided information, a request and consultation process specific to their choice. Choices can include: a synchronous review, an asynchronous review, a pathology review, and an asynchronous and pathology review. Other types of choices and combinations of choices are possible and the four provided herein are exemplary to illustrate preferred embodiments.

A synchronous review includes real time, for example, a real time face-to-face interactive video appointment between a patient and his referring physician and/or other health care specialist. Request and Consultation steps within the system may include providing the following to the patient:

i. The patient selecting which specialist he/she would like based on a description of the medical doctor and their specialist.
ii. The patient signing a release of information.
iii. The patient tiling out a Health History questionnaire.
iv. The patient providing Initial diagnosis (if any).
v. The patient uploading documents pertinent to medical records, imaging lab results, passport identification, and the like.
vi. Confirmation page receipt is given confirming appointment type, name and specialty of selected MD and initial diagnosis. Can be printed or emailed.
vii. Obtaining payment via credit card or referring physician through the portal.
viii. Scheduling the consultation via an online scheduler.
ix. Providing a registration receipt to email or print.
x. On the scheduled date of the consultation, the virtual second opinion consultation takes place. It is expected that a patient is on-site with their referring physician
xi. Following the consultation, the patient, referring physician and US-based specialist fill out a quality survey.
xii. Within 5 days of the consultation, the, for example, US-based specialist fills out a report and uploads it to the portal Patient and referring physician are notified via email and can access report of findings.

An asynchronous review includes a medical record review only by the second opinion specialist and would not provide real time face-to-face interaction. Request and Consultation steps within the system for an asynchronous review may include providing the following to the patient.

i. Patient selects which specialist he/she would like based on a description of the MD and their specialty.
ii. Patient signs a release of information.
iii Required demographic information is collected
iv. Health History questionnaire is filled out.
v. Initial diagnosis is documented (if any).
vi Patient uploads documents pertinent to medical records, imaging lab results, and passport identification.
vii. Confirmation page receipt is given confirming appointment type, name and specialty of selected MD and initial diagnosis. Can be printed or emailed.
viii. Payment is obtained via credit card or referring physician through the portal.
ix. Customer education for expectations takes place.
x. Registration receipt is available to email or print.
xi. Within 5 days of the consultation request, the US-based specialist fills out a report and uploads it to the portal. Patient and referring physician are notified via email and can access report of findings.

A pathology review can include previous medical pathology reports and documentation as well as patient samples (tissue blocks and/or slides) of body tissue for diagnostic purposes. Request and Consultation steps within the system for a pathology review may include providing the following to the patient i. Patient prints off a mailing label and packing slip.
ii. Patient electronically signs a release of information.
iii. Required demographic information is collected.

iv. Health History questionnaire is filled out.
v. Confirmation page receipt is given confirming appointment type, name and specialty of selected MD and initial diagnosis Can be printed or emailed.
vi. Payment is obtained via credit card or referring physician through the portal.
vii. Registration receipt is available to email or print
viii. Within 5 days of receiving the package for pathology review, the pathologist fills out a report and uploads it to the portal. Patient and referring physician are notified via email and can access report of findings.

An asynchronous and pathology review can include previous medical pathology reports and documentation as well as patient samples (tissue blocks and/or slides) of body tissue for diagnostic purposes and medical record review by a second opinion specialist. This feature of the system would NOT include real time face-to-face interaction. Request and Consultation steps within the system for a pathology and asynchronous review may include providing the following to the patient:

i. Patient selects which specialist he/she would like based on a description of the MD (health professional) and their specialty.
ii. Patient electronically signs a release of information.
iii. Required demographic information is collected.
iv Health History questionnaire is filled out.
v. Initial diagnosis is documented (if any).
vi. Patient uploads documents pertinent to medical records, imaging lab results, and passport identification.
vii. Confirmation page receipt is given confirming appointment type, name and specialty of selected MD and initial diagnosis. Can be printed or emailed.
viii. Payment is obtained via credit card or referring physician through the portal.
ix. Customer education for expectations takes place.
x. Registration receipt is available to email or print.
xi. Within 5 days of the consultation, the second opinion specialist fills out a report and uploads it to the portal. Patient and referring physician are notified via email and can access report of findings.

FIG. 13 represents an embodiment of the present system, methods and devices that can be deployed including use of a device such as a computing device or integrated into and as part of a telemedicine cart. The steps below are in a typical order of how a patient would access a consult. It is noted that this is the preferred order, though other orders of steps are possible within the scope of the embodiments. Some items are to be completed upon sign up only (namely steps 1310 (sign up), 1312, 1216, 1320 and 1322). The remaining items/steps may be completed each time a patient requests a second opinion from the second opinion platform. Note that step 1310 would be for signing into the platform once the sign up step has been initially completed.

Accordingly, as shown in FIG. 13, the second opinion platform 1300 first initiates as a sign up at step 1310. The next steps would be to create an account at step 1312, accepting terms and conditions at step 1314, receive and respond to an activation e-mail at step 1316, signing in at step 1318, providing customer identification at step 1320, and then proceeding to account activation, login and customer identification assignment at step 1322.

Thereafter from the first initiation of the second opinion platform 1300, at step 1310 the system would provide the user to just choose sign in at step 1310, accept the terms and conditions at step 1314, and be signed in at step 1318, then proceeding to the welcome landing page at step 1324. Next the user can be moved through an acknowledgement page 1326, how to request a telehealth consultation at step 1328, a review of documents requirements at step 1330, referring physician (or other health care professional) information 1332, and from there providing selections from (for exemplary purposes only) four telehealth consult types; Pathology Review, Synchronous, Asynchronous; or Asynchronous and Pathology Review. It is noted that the illustrated data flow shows what happens when the user selects one of four consultant types by splitting each into one of four consultation type columns as follows: Pathology Review 1348, Synchronous 1350; Asynchronous 1352; or Asynchronous and Pathology Review 1354. Steps that extend through or across than one column would occur independently in each column but are shown once across the columns as an expedient.

If the user selects a Pathology Review 1348 consult, they are provided instructions to obtain the review in step 1336 then the system proceeds to step 1356. If the user selects a Synchronous 1350 consult they are provided search options for a pre-approved health care expert in steps 1338, 1344 and 1346. Then the system proceeds to step 1356. If the user selects an Asynchronous 1352 consult, they are advanced at 1340 to step 1356. If the user selects an Asynchronous consult and a Pathology Review 1354 they are provided instructions to obtain the review in step 1342 then the system proceeds to step 1356.

Once the user advances past the instructions or decisions from steps 1336, 1338, 1344, 1346, 1340 and 1342, irrespective of the chosen consulting type, the user proceeds through steps 1356, 1358, 1360, 1362, 1364, 1366 and 1368 and next picks one of payments at step 1370 (facility code) or 1372 (self-pay). Accordingly, the system requires the user to provide an authorization to treat and a release of information at step 1356. Next, the system requests required demographic information at step 1358, health questionnaire information at step 1360, and diagnosis at step 1362. Next the system prompts the user to upload predetermined documentation at step 1364, followed by generating a confirmation page receipt at step 1366. Next the system moves to a payment method screen at step 1368 and can allow a user to select, for example, a payment by a facility code 1370 or self-payment at step 1372.

After the user has selected between a payment facility code 1370 or self-payment at step 1372 for a Pathology Review 1348 consult, the system can issue the user a registration receipt 1388. As discussed above, for example, within 5 days of receiving the package for pathology review, the pathologist can fill out a report and upload it to the system via a portal. The systems generates via email or similar communication a notification to the Patient and referring physician to access the report of findings.

After the user has selected between a payment facility code 1370 or self-payment at step 1372 for a Synchronous 1350 consult, the user can be prompted for customer scheduling education at step 1374 followed by scheduling a health professional consultation at step 1376. The system issues the user a registration receipt 1388.

Figure 13C:
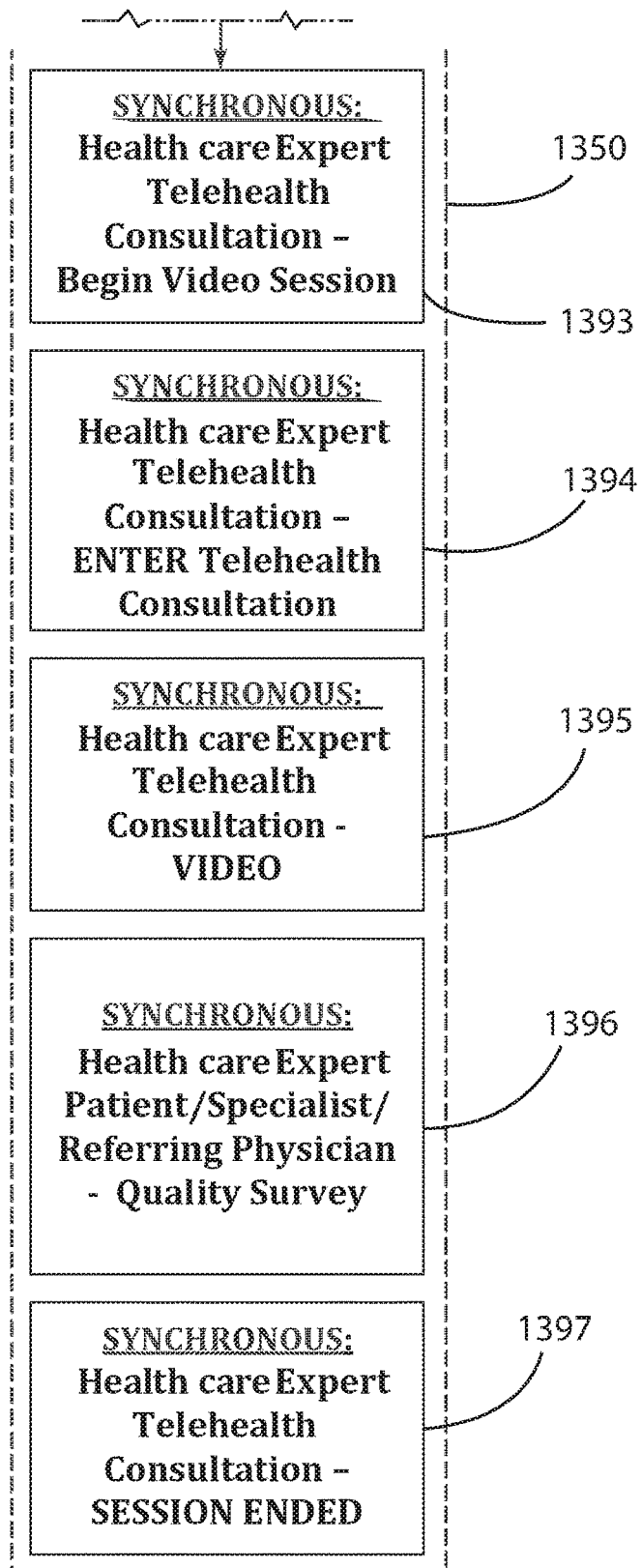

Next, the system begins the video the synchronous consultation at step 1393 as determined in step 1376, followed by entering the consult at step 1394 at consultation date 1390. Next (FIG. 13C) the system can provide a synchronous video link between, for example, the consultant, the health care provider and the patient at step 1395. Following the video consultation at step 1395, the system can prompt a user to complete a quality survey at step 1396 followed by closing the video session at step 1397. As discussed above, for example, within 5 days of the consultation, the second opinion specialists can fill out a report and upload it to the system via a portal. The systems generates via email or similar communication a notification to the user/patient and referring physician to access the report of findings.

After the user has selected between a payment facility code 1370 or self-payment at step 1372 for an Asynchronous 1352 consult, the user is prompted for customer scheduling education at step 1380. The system issues the user a registration receipt 1388. As discussed above, for example, within 5 days of the consultation, the second opinion specialists can fill out a report and upload it to the system via a portal. The systems generates via email or similar communication a notification to the user/patient and referring physician to access the report of findings.

After the user has selected between a payment facility code 1370 or self-payment at step 1372 for an Asynchronous consult and Pathology Review consult 1354 consult, the user is prompted for customer scheduling education at step 1384. The system issues the user a registration receipt 1388. As discussed above, for example, within 5 days of the consultation, the second opinion specialists and pathologist can fill out a report and upload it to the system via a portal. The systems generates via email or similar communication a notification to the Patient and referring physician to access the report of findings.

As described herein, the healthcare providers may provide further follow-up as need for patient care.

Figure 14:
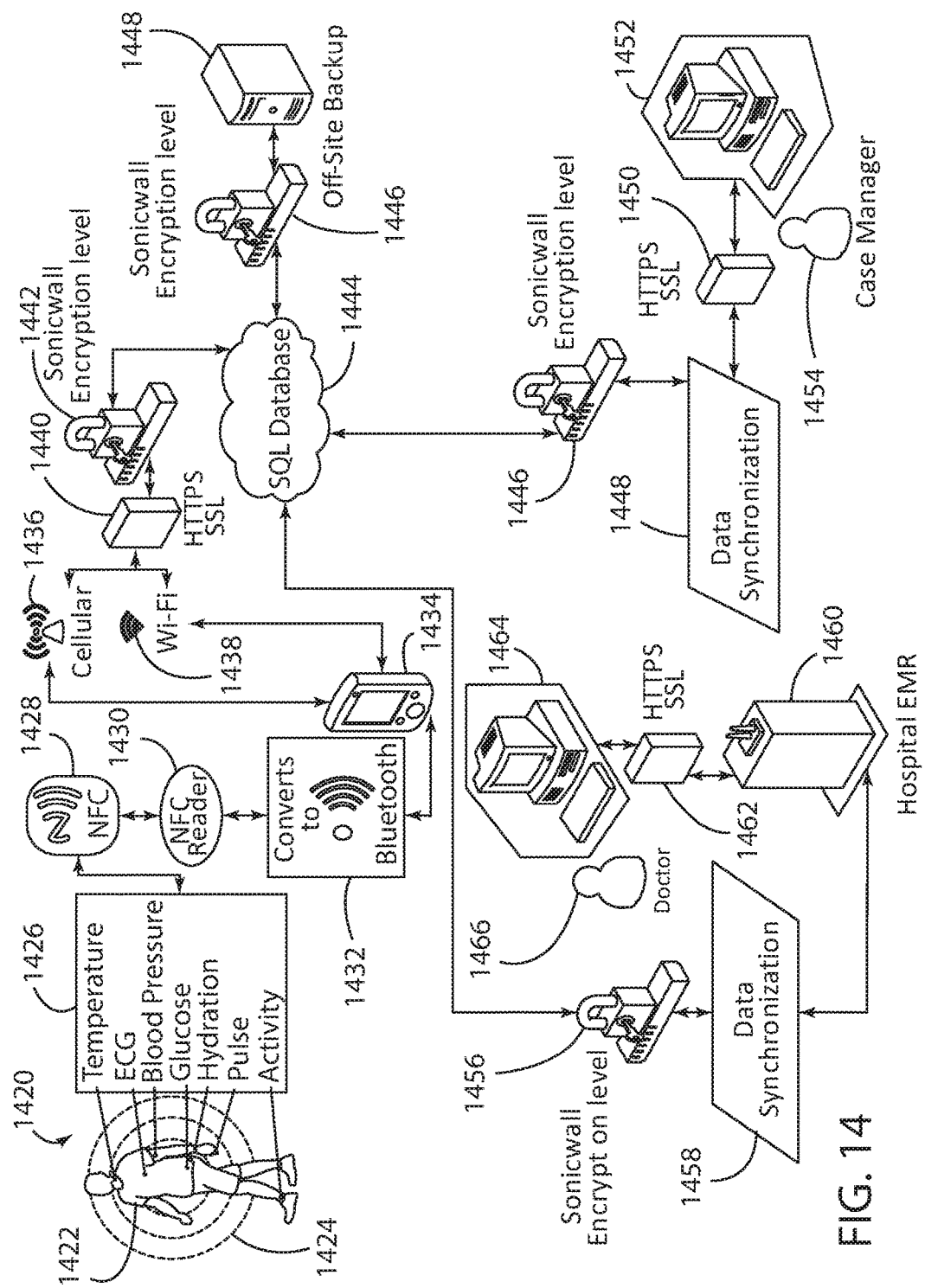
FIG. 14 illustrates an exemplary system and method for use in implementing methods, techniques, devices, apparatuses, systems, servers, sources and the like, in accordance with some of the present embodiments detailing input from a patient's biosensors.

FIG. 14 illustrates an exemplary system and platform for use in implementing methods, techniques, devices, apparatuses, systems, servers, sources and the like, in accordance with some of the present embodiments detailing input from a patient's biosensors. As illustrated in FIG. 14, one embodiment of this system and platform is generally indicated at 1420 having a user/patient 1422 communicatively connected to platform 1420 via at least one biosensor 1426. A biosensor can be a sensor that can sense the patient's state in real time or recorded over a period of time or the environment around the patient. Examples of these types of sensors can include a patient 1422's temperature, ECG, blood pressure, glucose levels, pulse, activity levels, and the like and any combination thereof. Sensors could also include ambient temperature, time of day, light, humidity, and the like and combinations thereof.

A patient's near field 1424, i.e., an immediate area around the patient, can allow for connectivity with platform 1420 using near field communications. As an example, Near Field Communication (NFC) is a short-range wireless connectivity standard (Ecma-340, ISO/IEC 18092) that uses magnetic field induction to enable communication between devices when they are touched together, or brought within a few centimeters of each other in zone 1424. The standard specifies a way for the devices to establish a peer-to-peer (P2P) network to exchange data. After the P2P network has been configured, another wireless communication technology, such as Bluetooth, cellular, or Wi-Fi Connectivity, can be used for longer range communication or for transferring larger amounts of data. (See generally, http://searchmobilecomputing.techtarget.com/definition/Near-Field-Communication)

As shown in FIG. 14, an NFC device 1428 and the system NFC reader 1430 may be used to connect the biosensor output (and in some embodiments to receive system output) with the platform 1420. It is noted that while NFC technology is described herein, other types of wireless communication or even wired communication are possible within the scope of the present embodiments.

Platform 1420 may have an NFC convertor 1432, which can convert the NFC communication into, for example, a wireless technology such as known under the trade name BLUETOOTH. It is again noted that while BLUETOOTH technology is described herein for this aspect of the present embodiment, other types of wireless communication or even wired communication are possible within the scope of the present embodiments. It is likewise noted that any device in the embodiments described herein would not be limited to specific wireless or wired communications unless specifically described as such.

Next the BLUETOOTH communication from the biosensors can be received from a further device, such as a mobile phone, tablet and the like, which is communicatively connected to a cell tower 1436 or the Internet via a WI-FI connection 1438. From here the biosensor input (or the output to the biosensor) can enter the Internet via various communications protocols, such as HTTPS SSL 1440 then to a SONICWALL encryption level at 1442. It is noted that for purposes of clarity the data flow is described as shown flowing from the biosensor. It is noted that data can similarly flow in reverse and generated to be received by the biosensor or within other components of the systems methods and devices described herein.

Next the input from the biosensor 1426 can be saved to a platform 1420 database, such as an SQL database 1444. Structured Query Language (SQL) is a standard computer language for relational database management and data manipulation. SQL is used to query, insert, update and modify data. Most relational databases support SQL, which is an added benefit for database administrators (DBAs), as they are often required to support databases across several different platforms. It is noted though that other types of platforms would be possible. The illustrated SQL database can be communicatively be connected to the patient's health care provider 1466, the patient's case manager 1454, and to the systems off-site backup system and device 1448.

As the biosensor 1426 information proceeds from database 1444 to backup 1448, it can pass through a sonic wall encryption level 1446.

As the biosensor 1426 information proceeds from database 1444 to health care provider 1466, it can pass through a sonic wall encryption level 1456 and data synchronization 1458. Next the biosensor data can then proceed to a hospital EMR 1460, then into the Internet via HTTPS SSL communications protocols 1462 to health care professional's computing device 1464. Device 1464 can include a personal computer, a tablet computer, a gateway device, smart phone, and the like and combinations thereof.

As the biosensor 1426 information proceeds from database 1444 to the patient case manager 1454, it can pass through a sonic wall encryption level 1446 and data synchronization 1448, then into the Internet via HTTPS SSL communications protocols 1450 to case manager's computing device 1452. Again, device 1452 can include a personal computer, a tablet computer, a gateway device, smart phone, and the like and combinations thereof.

It is also noted that the present biosensor information may also be integrated into the other systems, methods and apparatuses to provided warnings, scheduling and notifications and other features as described herein.

An optional radiology image viewer application can also be added as part of the features of the present systems, methods and present telemedicine platform devices. In one exemplary approach, a web based application can be based on remote or network based real-time access to Digital Imaging and Communications in Medicine (DICOM)

images/data files. DICOM is the standard for the communication and management of medical imaging information and related data (e.g., CT Scans, X-rays, MRI, other types radiology files and the like). Real time collaboration with all applications described herein can also be configured for manual or automatic entry and storage of patient diagnostic data in a HIPAA compliant encrypted environment In the present application. This feature allows for health care providers to collaborate among themselves or with the patient with real-time DICOM image viewing. This feature can also overlay with concurrent videoconferencing feature also included as part of the telemedicine platform. The videoconferencing can include DICOM image sharing among multiple users' browsers using a cloud based server or a local machine. In some applications, multiple portals can be opened to allow additional peripheral devices described herein, such as cameras, microphones and the like.

DICOM images can be loaded and viewed remotely by healthcare specialist or patient. Screen shots are shown at FIGS. 15-22 from an exemplary embodiment of the present application. In FIG. 17 using the "Store/Upload" feature, images may be added. Additional functionality, like measuring, rotation, etc. to the images, can also be provided as will be described below.

Accordingly, as shown in FIG. 6 above, once the physician's authorization to review data for a specific patient is confirmed, the DICOM data can be transmitted in encrypted form to physician device 38. At step 1016, physician device 38 can include executable code (which may be provided by content manager server 44) to allow for the decrypting of encrypted patient DICOM information. The patient DICOM information can then be display on physician device 38 to be viewed by the physician at step 1018. See also, FIG. 14, Device 1464. Upon access to the system, a medical professional 1466 can see, by way of example, an Icon based screen is shown in FIG. 15.

Turning now to the Figures, FIGS. 15-22 show user interface screens according to one approach to the present DICOM image viewing application.

Figure 15:
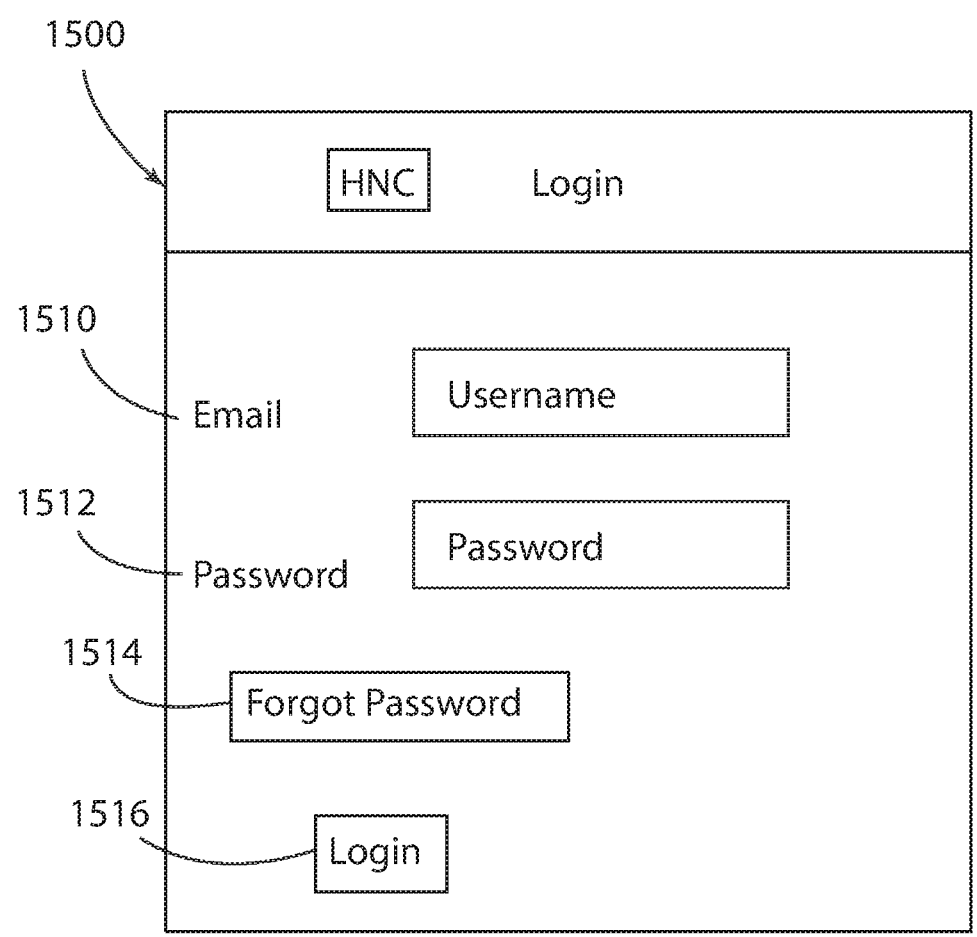

FIG. 15 illustrates an exemplary Login in screen to access an exemplary application to view DICOM records and the like. Sign in screen 1500 allows access to the application with login credentials such as e-mail 1510 and Password 1512. A "Forgot Password" option 1514 is also provided. Once the credentials are entered the user may use the "Login" 1516 button to access the application.

Figure 16:
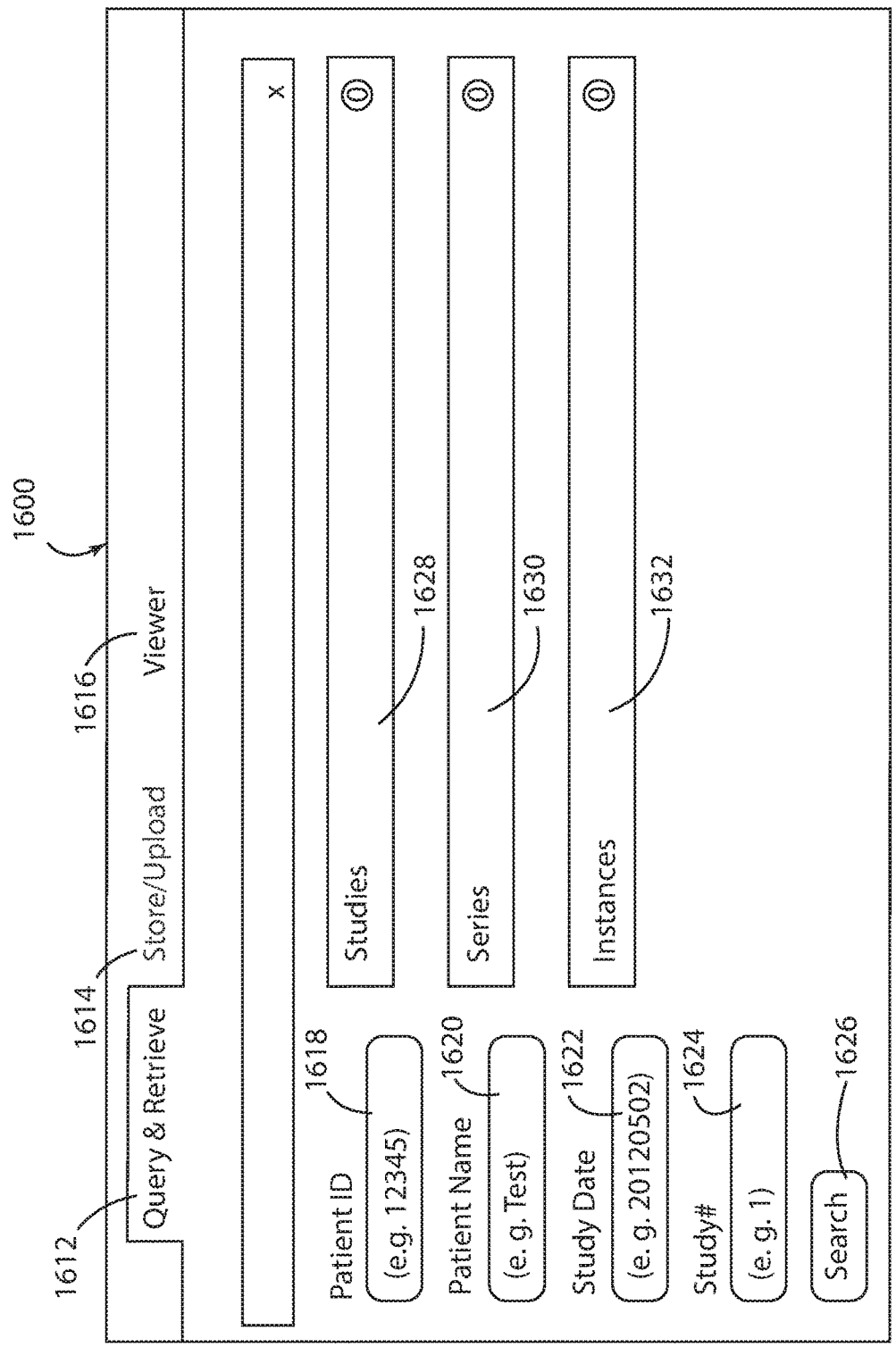
FIG. 16 illustrates an exemplary homepage for the application to view DICOM records and the like of FIG. 15 defaulting to the "Query and Retrieve" tab.
Figure 17:
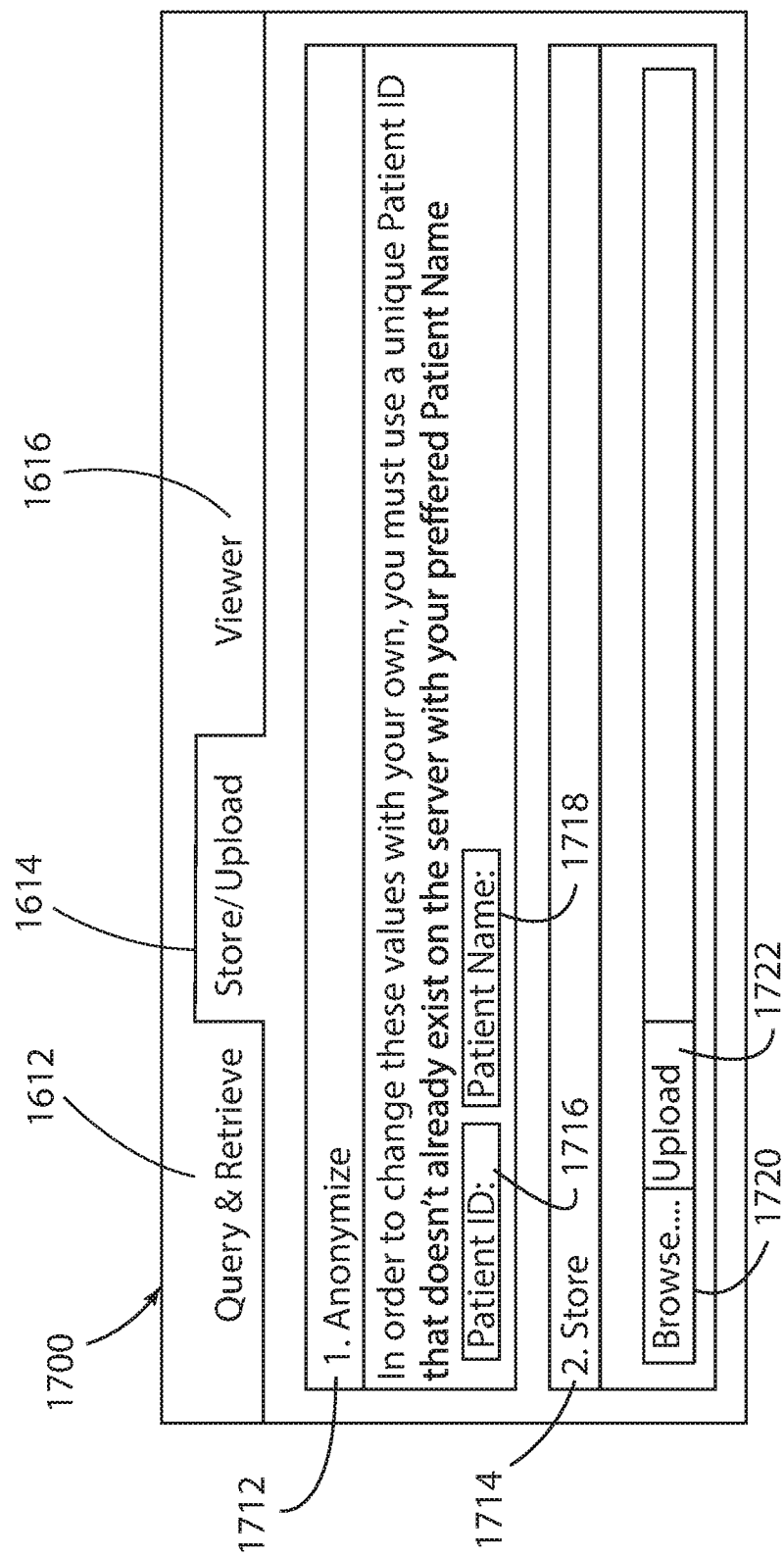
FIG. 17 illustrates an exemplary view for the homepage of FIG. 16 to view DICOM records when the "Store/Upload" tab is selected.

FIG. 16 illustrates an exemplary default homepage 1600 for the application to view DICOM records and the like of FIG. 15 defaulting to the "Query and Retrieve" tab 1612. Other tabs include a "Store/Upload" tab 1614 and a "Viewer" tab 1616 described below Under the "Query and Retrieve" tab 1612 a user may enter identifiers to locate a patient's DICOM images including: Patient ID (system unique identifier, e.g., social security number) 1618; Patient name 1620; Study date 1622; Study #1624 (Medical series number, Serial number, etc.). The system will perform a search for the identified records by tapping the Search command button 1626. Once the search has been execute, identified records can be retrieved by Studies 1628 (listing DICOM images by e.g., affected body part; Series 1630 (all the studies with the series, e.g., different angles captured and Instances 1632 (e.g., by clicking a series).

FIG. 17 illustrates an exemplary view for the homepage 1700 of FIG. 16 to view DICOM records when the "Store/Upload" tab is selected. The system can anonymize data when shared or uploaded by requiring entry or removal of the Patient ID and/or the Patient name. Usually the DICOM data has the patient information as port of its meta-data. See FIG. 18. Accordingly, the screen provides, for example, an Anonymize 1712 feature as to Patient ID 1714 and Patient name 1716. Store 1718 feature allows options to Browse 1720 or Upload 1722 DICOM images.

Figure 18:
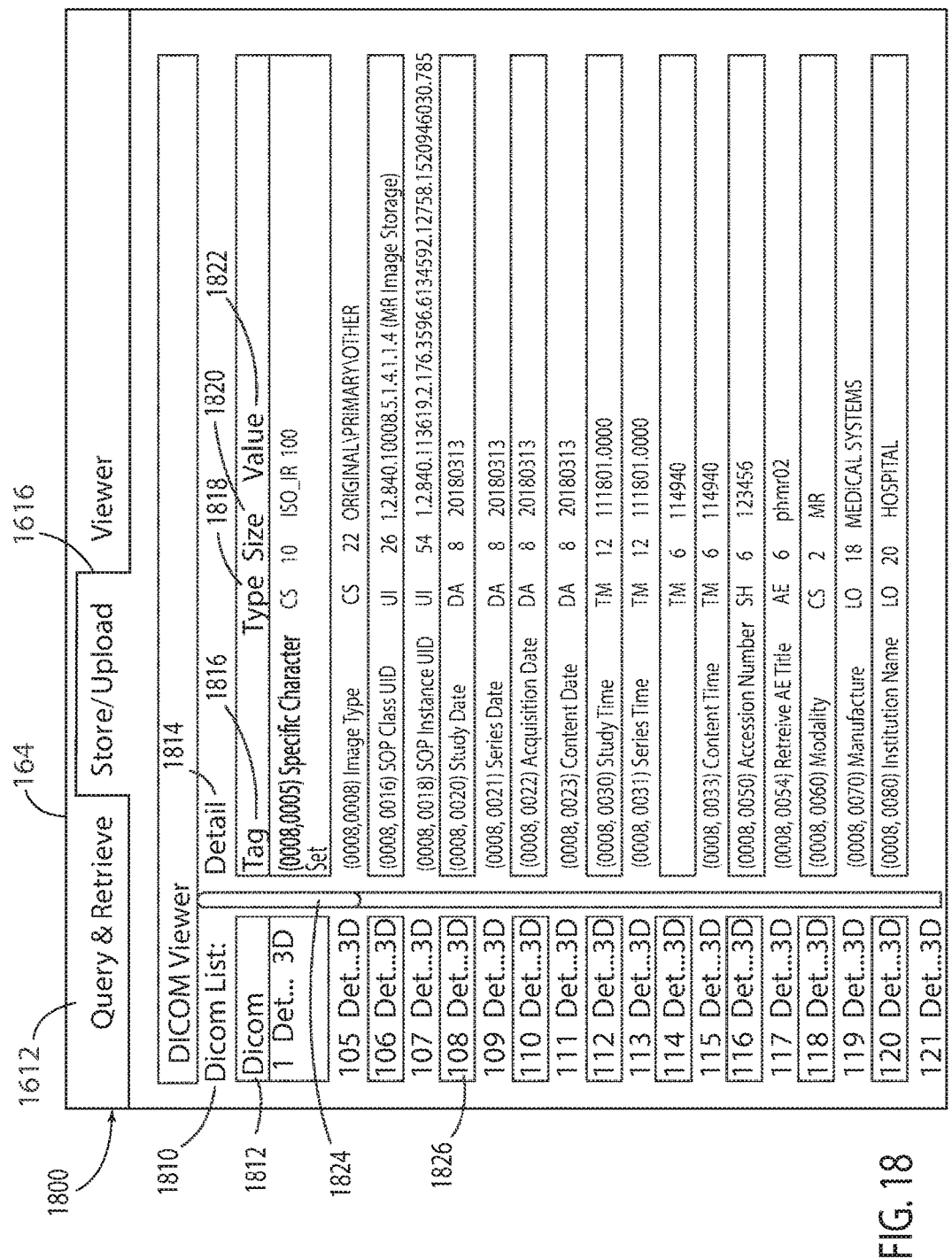
FIG. 18 illustrates an exemplary view for the homepage of FIG. 16 to view DICOM records when the "Viewer" tab is selected.

FIG. 18 illustrates an exemplary view for a homepage 1800 of FIG. 16 to view DICOM records when the "Viewer" tab is selected or when other routes to access metadata information related to the DICOM image is requested by a user. This screen can provide, for example, a DICOM list 1812, DICOM hyperlink detail 1814 (such as TAG 1816, TYPE 1818, SIZE 1820, VALUE 1822, a scroll bar 1824 and a link 1826 to a specific DICOM image (DET=detail; 3d=3 dimensional).

Figure 19:
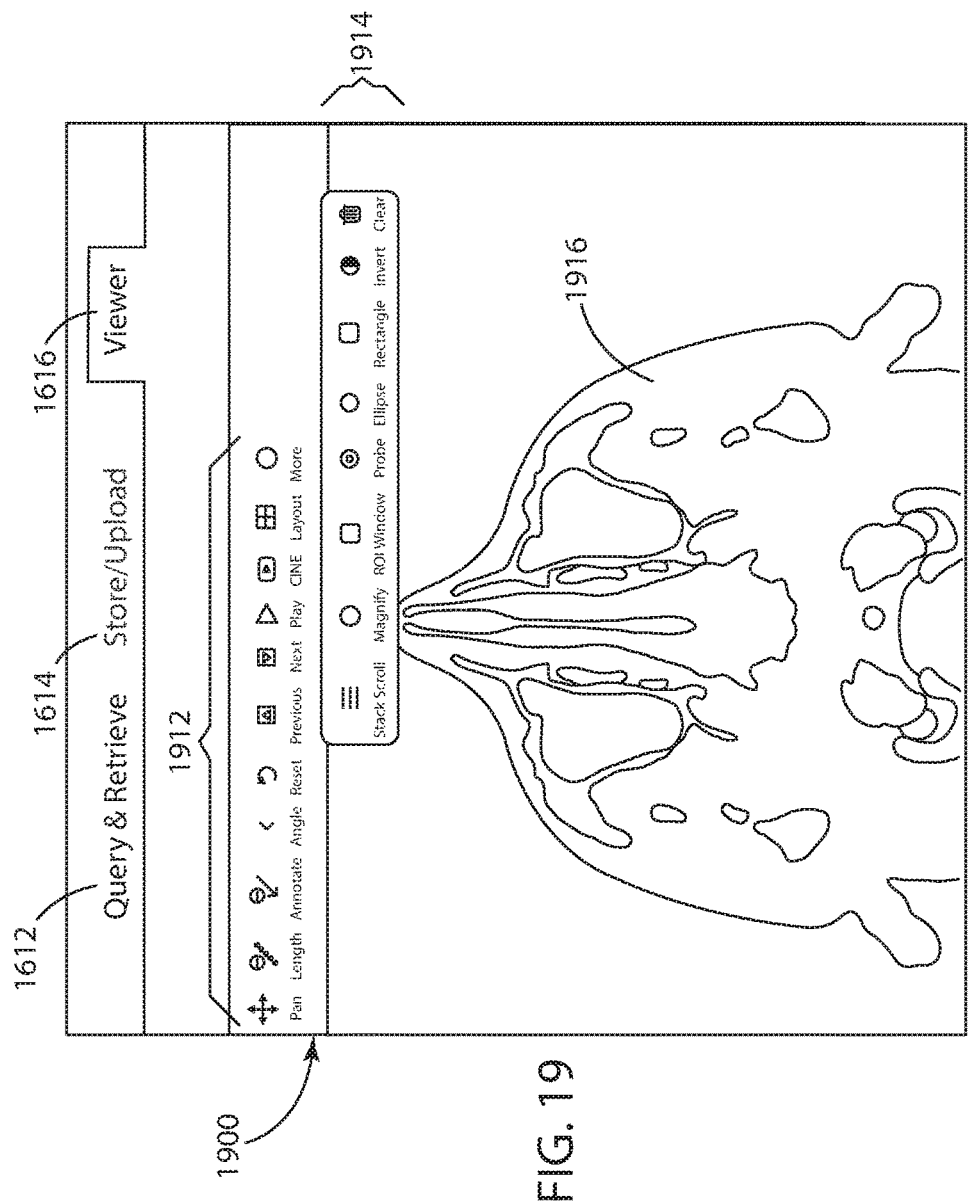
FIG. 19 illustrates an exemplary schematic view of a selected DICOM record selected from DICOM list of FIG. 18.

FIG. 19 illustrates an exemplary schematic view of a selected DICOM record selected from DICOM list of for example, FIG. 18. A DICOM Viewer 1900 can provide image treatment 1912 (such as PAN, length measurements, annotations, angle adjustment, reset to original image, next image, PLAY images, video, and the like), image stacking options 1914 can be included (, stack, scroll, magnify, ROI (Region of Interest) window, Probe, ellipse, rectangle selection, invert and clear) to display DICOM image 1916.

Figure 20:
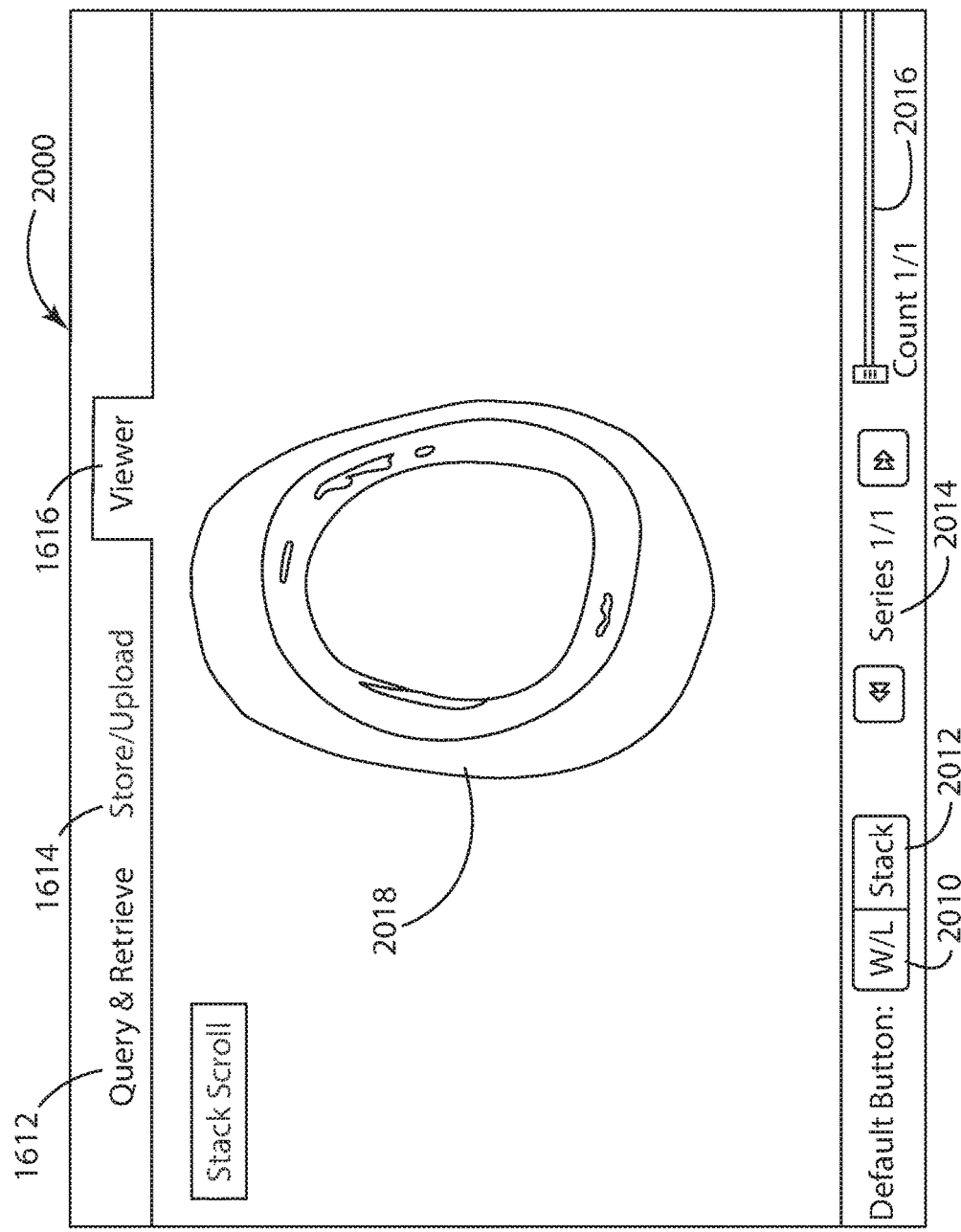
FIG. 20 illustrates an alternate exemplary schematic view of a selected DICOM record selected from DICOM list of FIG. 19 and the 'Stack Scroll' button is selected.

FIG. 20 an alternate exemplary schematic view of a selected DICOM record 2000 selected from DICOM list of FIG. 19 with the 'Stack Scroll' button is selected. Features of this screen may include Window Level 2010, Stack (See e.g., FIG. 19) 2012; Series Selection 2014; Scroll bar for image within series 2016 to affect the display of DICOM image 2018.

Figure 21:
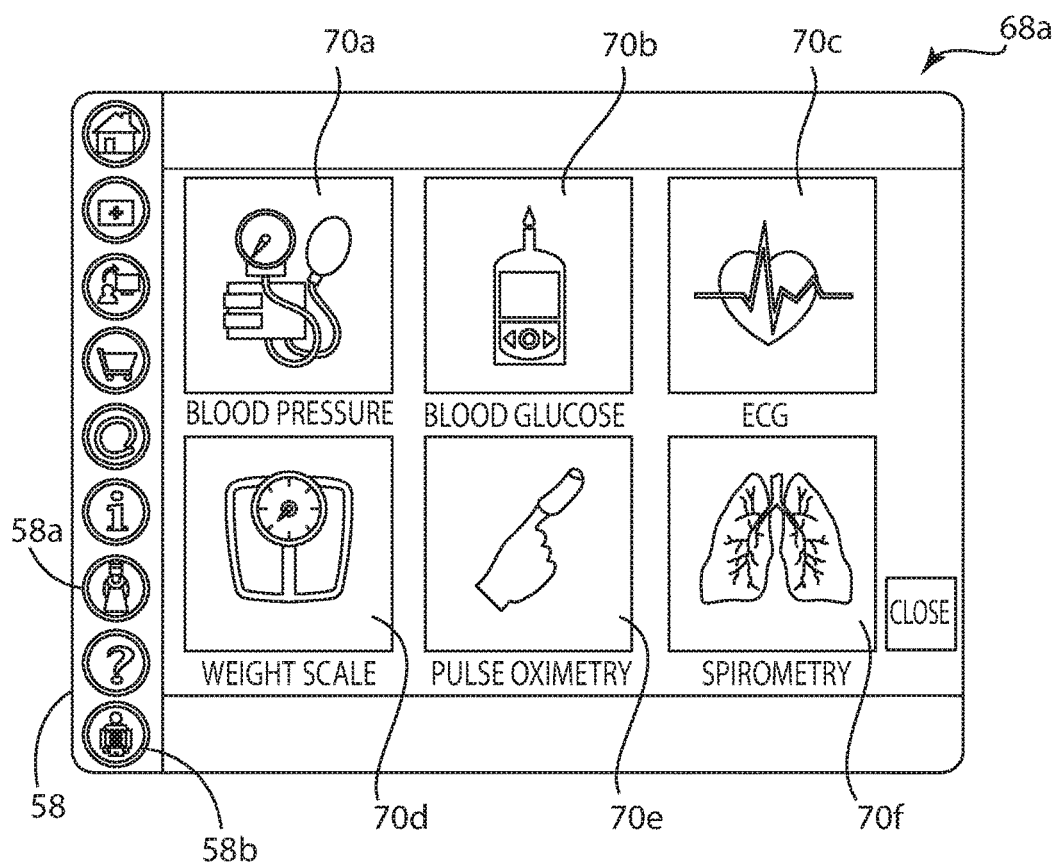

FIG. 21 illustrates an alternate exemplary Login in screen 68 *a* (Cf., FIGS. 4*a* and 16) with a graphical user interface screen to access an exemplary applications including an application to view DICOM records and the like. As shown, this screen can provide a system toolbar 58; nurse application 58 *a*; DICOM viewer application 58 *b*; user home screen 68 *a* and graphical interface button to launch specific application 70 *a-f*.

Figure 22:
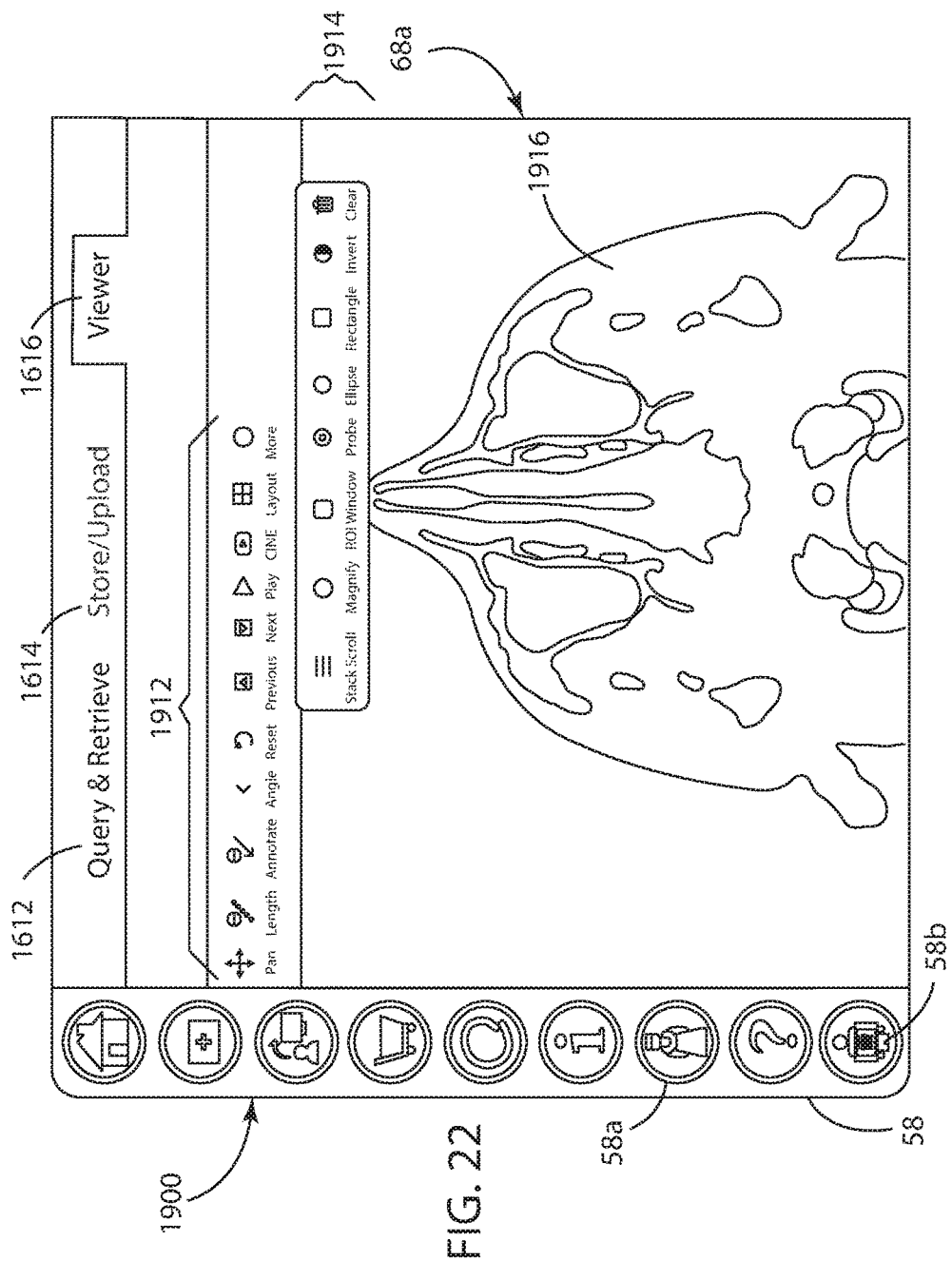
FIG. 22 illustrates the graphical user interface screen of FIG. 21 showing an exemplary schematic view of a selected DICOM record selected from a patient specific DICOM list.

FIG. 22 illustrates the graphical user interface screen of FIG. 21 when icon 58 *b* is selected showing an exemplary schematic view of a selected DICOM record selected from a patient specific DICOM list.

Figure 23:
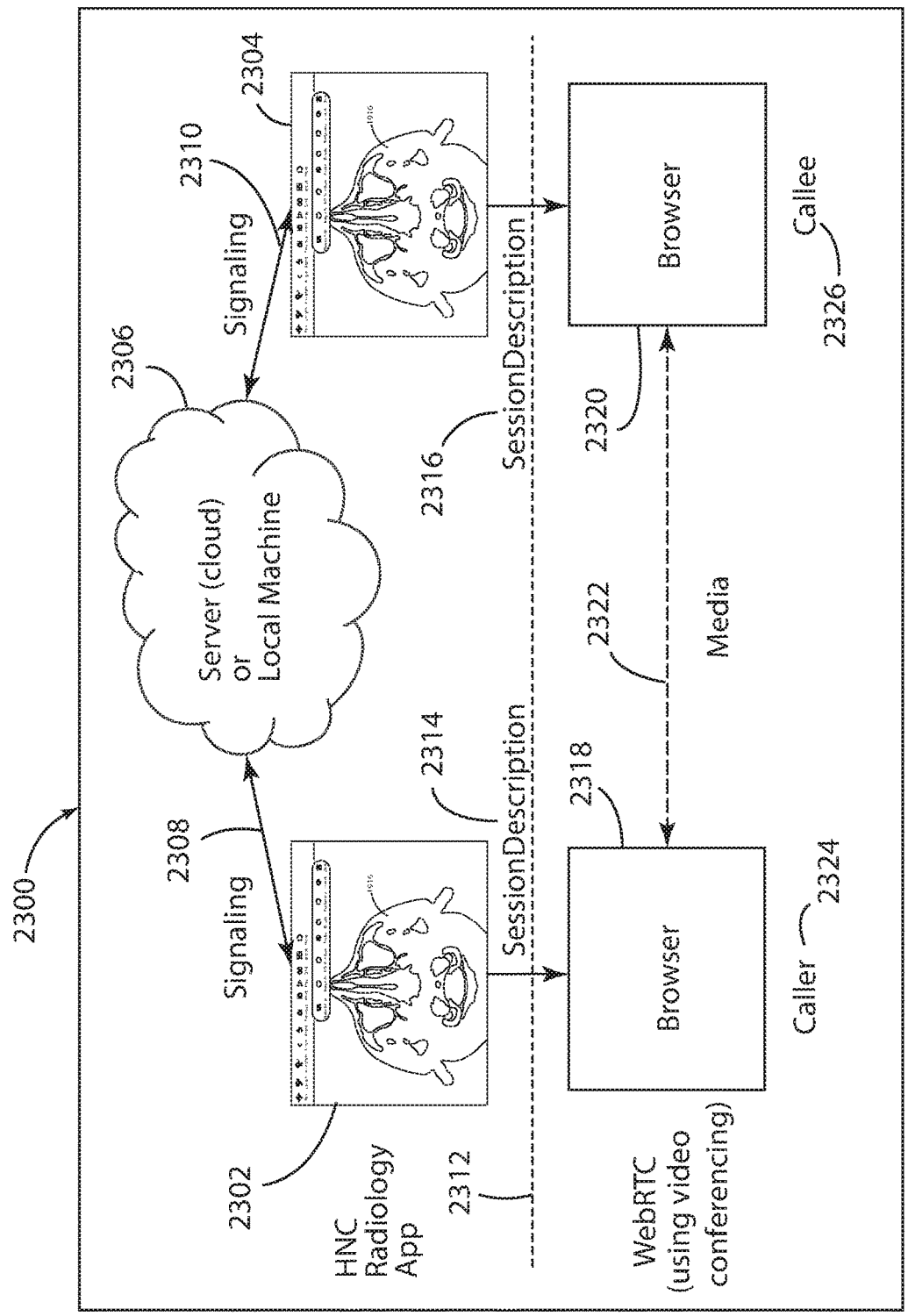
FIG. 23 illustrates an exemplary schematic of an optional video conferencing capability within the DICOM viewer application.

FIG. 23 illustrates an exemplary schematic of an optional video conferencing capability within the DICOM viewer application. This application adds a WebRTC functionality to the DICOM application. WebRTC is a free, open-source code to provide web browsers and mobile applications real-time communication via application interfaces. This functionality will add real time communication to the application which can allow health care professional to interact in real-time using the DICOM viewer feature. This functionality allows users to share real time interactive communication. This WebRTC application can provide real-time communication, sharing, screen recording, messaging, etc. capabilities via application program interfaces (APIs) to the present Radiology DICOM application. Accordingly, multiple doctors can view, edit and provide real time opinion on any given DICOM image or case. This is mostly going to be backend process, so there won't be special screen shot for it. We can discuss more on call if required and explain to you in details.

As shown in FIG. 23, this Video conferencing option for DICOM viewer application 2300 options can provide a caller generated screen with DICOM viewer app loaded 2302 and a simultaneous callee generated screen from caller screen 2304 connected via server, cloud or local machine (server) 2306. Also this provides data transfer to/from server of caller 2308 and data transfer to/from server of callee 2310 to deliver to browser 2312 via a session description to caller to share the session 2314 and session description to callee to share the session 2316. This allows for a caller screen with WebRTC application 2318 and callee screen 2320 via media transfer 2322 to caller 2324 and callee 2326.

Figure 12:
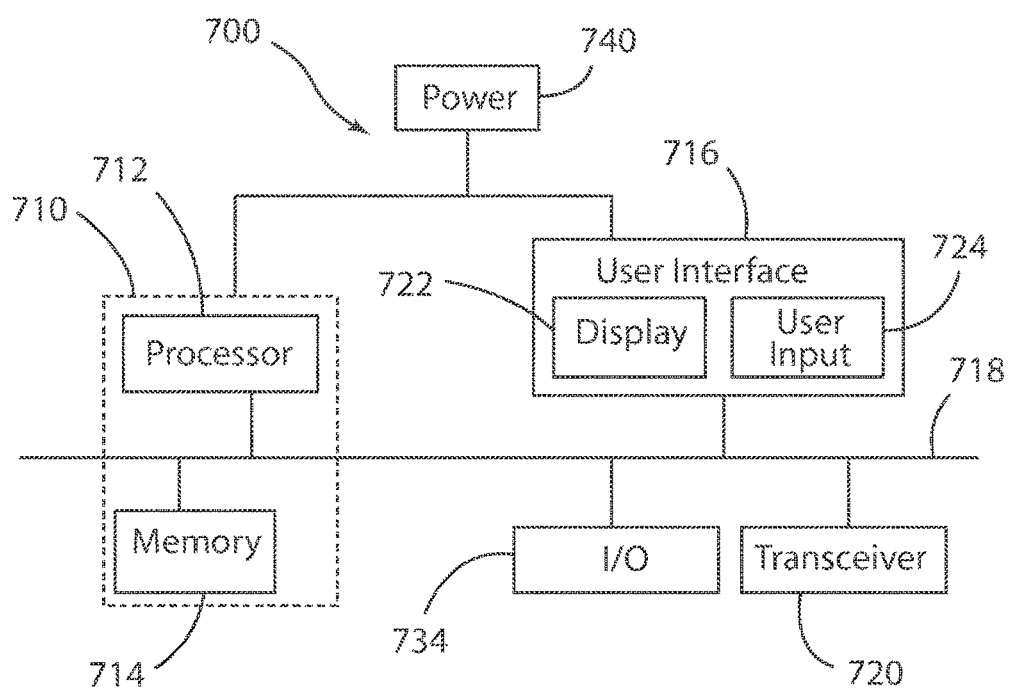
FIG. 12 illustrates an exemplary system for use in implementing methods, techniques, devices, apparatuses, systems, servers, sources and the like, in accordance with some of the present embodiments.

In a general illustration, the present invention can be realized as methods or systems in hardware, software, or a combination of hardware and software of a computing device system including a computing device network system as shown schematically in FIG. 12. The present invention can be realized in a centralized fashion in one computing device system or in a distributed fashion where different elements are spread across several computing device systems. Any kind of computer system, or other apparatus adapted for carrying out the methods described herein, is suited.

A typical combination of hardware and software may include a general purpose computer system with a computer program that, when being loaded and executed, controls the computer system such that it carries out the systems and methods described herein. The present invention may be voluntarily embedded in a computing device program product (or any computing device useable medium having computer readable program code embodied therein), which comprises all the features enabling the implementation of the methods and systems described herein and which when loaded in a computing device system is able to carry out these systems and methods. The present invention may be embedded in a computing device program product by a manufacturer or vendor of the computing device (or any computing device useable medium having computer readable program code embodied therein), which comprises all the features enabling the implementation of the methods and systems described herein and which when loaded in a computer system is able to carry out these systems and methods, and is voluntarily turned off or on by the user. The present invention may be embedded in a computer program product by a manufacturer or vendor of the computer (or any computer useable medium having computer readable program code embodied therein), which comprises all the features enabling the implementation of the methods and systems described herein and which when loaded in a computer system carries out these systems. Computer program or computer program product in the present context means any expression, in any language, code or notation, of a set of instructions intended to cause a system having an information processing capability to perform a particular function either directly or after either or both of the following: (a) conversion to another language, code or notation, and (b) reproduction in a different material or electronic form.

Further, the processes, methods, techniques, circuitry, systems, devices, functionality, services, servers, sources and the like described herein may be utilized, implemented and/or run on many different types of devices and/or systems. Referring to FIG. 12, there is illustrated an exemplary system 700 that may be used for many such implementations, in accordance with some embodiments. One or more components of the system 700 may be used for implementing any circuitry, system, functionality, apparatus or device mentioned above or below, or parts of such circuitry, functionality, systems, apparatuses or devices, such as for example any of the above or below mentioned computing device, the systems and methods of the present invention, request processing functionality, monitoring functionality, analysis functionality, additionally evaluation functionality and/or other such circuitry, functionality and/or devices. However, the use of the system 700 or any portion thereof is certainly not required.

By way of example, the system 700 may comprise a controller or processor module, memory 714, and one or more communication links, paths, buses or the like 718. Some embodiments may include a user interface 716, and/or a power source or supply 740. The controller 712 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, programs, content, listings, services, interfaces, logging, reporting, etc. Further, in some embodiments, the controller 712 can be part of control circuitry and/or a control system 710, which may be implemented through one or more processors with access to one or more memory 714. The user interface 716 can allow a user to interact with the system 700 and receive information through the system. In some instances, the user interface 716 includes a display 722 and/or one or more user inputs 724, such as a buttons, touch screen, track ball, keyboard, mouse, etc., which can be part of or wired or wirelessly coupled with the system 700.

Typically, the system 700 further includes one or more communication interfaces, ports, transceivers 720 and the like allowing the system 700 to communication over a communication bus, a distributed network, a local network, the Internet, communication link 718, other networks or communication channels with other devices and/or other such communications or combinations thereof. Further the transceiver 720 can be configured for wired, wireless, optical, fiber optical cable or other such communication configurations or combinations of such communications. Some embodiments include one or more input/output (I/O) ports 734 that allow one or more devices to couple with the system 700. The I/O ports can be substantially any relevant port or combinations of ports, such as but not limited to USB, Ethernet, or other such ports.

The system 700 comprises an example of a control and/or processor-based system with the controller 712. Again, the controller 712 can be implemented through one or more processors, controllers, central processing units, logic, software and the like. Further, in some implementations the controller 712 may provide multiprocessor functionality.

The memory 714, which can be accessed by the controller 712, typically includes one or more processor readable and/or computer readable media accessed by at least the controller 712, and can include volatile and/or nonvolatile media, such as RAM, ROM, EEPROM, flash memory and/or other memory technology. Further, the memory 714 is shown as internal to the system 710; however, the memory 714 can be internal, external or a combination of internal and external memory. Similarly, some or all of the memory 714 can be internal, external or a combination of internal and external memory of the controller 712. The external memory can be substantially any relevant memory such as, but not limited to, one or more of flash memory secure digital (SD) card, universal serial bus (USB) stick or drive, other memory cards, hard drive and other such memory or combinations of such memory. The memory 714 can store code, software, executables, scripts, data, content, lists, programming, programs, log or history data, user information and the like.

Some of the present embodiments may be installed on the computing device that receives data transaction requests from the computing device from an interface. The present embodiments can be configured to process data transaction requests received through the interface. Typically, the present embodiments can be communicatively connected to a communication network (e.g., a WAN, LAN, the Internet, etc.), and has the capability of completing the data transaction requests. The present embodiments can communicationally connect with one or more remote servers that are configured to provide information useful in determining the nature of one or more data transaction requests. The present embodiments can further, in some instances, complete a data transaction request through the interface.

Further, in some applications, the remote server is implemented through and/or includes a server cluster containing multiple servers that cooperatively operate and/or communicate to provide analysis functionality. In other instances, the remote server may be implemented in pan or fully on personal computer.

The present embodiments may further block access to the network access activity when the network access activity is considered an objectionable or non-compliant activity.

Third party recipients can access one or more reports in a variety of ways including, but not limited to, the report or reports being communicated by one or more of the remote servers, the third party having access to the remote server to request report, and other such methods. A request for a report can include viewing the report while the third party has access to the remote server.

In some implementations, monitoring software is installed on the computing device 1, and in some embodiments is part of the present embodiments. Additionally or alternatively, some or all of the monitoring and/or monitoring program is implemented at a remote server. In some applications, the monitoring software can be voluntarily installed on the computing device by a user. In other instances, the monitoring software can be pre-installed on the computing device.

In some embodiments, network access activity can includes, for example, access to one or more of the network activity from a group consisting of http, https, network news transfer protocols, file sharing programs, file transfer protocols, chat room access, peer to peer chats, game protocols, downloads of data, and electronic mail activity. The present embodiments can complete the data transaction request through the interface. In some implementations, the report can be made accessible by a third party recipient (e.g., via direct access through a server 10, e-mail, periodic reports, text alerts, etc.).

One or more of the embodiments, methods, processes, approaches, and/or techniques described above or below may be implemented in one or more computer programs executable by a processor-based system. By way of example, such a processor based system may comprise the processor based system 700, a computer, a server, a smart phone, a smart watch, a tablet, a laptop, etc Such a computer program may be used for executing various steps and/or features of the above or below described methods, processes and/or techniques. That is, the computer program may be adapted to cause or configure a processor-based system to execute and achieve the functions and/or functionality described above or below.

As an example, such computer programs may be used for implementing any type of tool or similar utility that uses any one or more of the above or below described embodiments, methods, processes, functionality, approaches, and/or techniques. In some embodiments, program code modules, loops, subroutines, etc., within the computer program may be used for executing various steps and/or features of the above or below described methods, processes and/or techniques. In some embodiments, the computer program may be stored or embodied on a computer readable storage or recording medium or media, such as any of the computer readable storage or recording medium or media described herein.

Accordingly, some embodiments provide a processor or computer program product comprising a medium configured to embody a computer program for input to a processor or computer and a computer program embodied in the medium configured to cause the processor or computer to perform or execute steps comprising any one or more of the steps involved in any one or more of the embodiments, methods, processes, functionality, approaches, and/or techniques described herein. For example, some embodiments provide one or more computer-readable storage mediums storing one or more computer programs for use with a computer simulation, the one or more computer programs configured to cause a computer and/or processor based system to execute steps comprising: receiving data through the present embodiments that receives data transaction requests, from a local computing device on which the present embodiments are implemented, through an interface; and processing, through the present embodiments, data transaction requests received through said interface. Some embodiments further comprise completing said data transaction requests through the present embodiments that is communicatively connected via a wide area network (WAN) to a remote server which is communicatively connected to said present embodiments; wherein said remote server is configured to provide information useful in determining a nature of said data transaction request. Some embodiments additionally or alternatively comprise monitoring network access activity of the local computing device, including network activity of applications installed on said local computing device, recording results of monitoring said Internet access activity within said remote server. Additionally, some embodiments further comprise completing a data transaction request, by the present embodiments, through an interface. Further, in some instances, the Internet access activity can include access to at least one Internet activity from a group consisting of http, https, network news transfer protocols, file sharing programs, file transfer protocols, chat room access, peer to peer chats, game protocols, downloads of data, and electronic mail activity.

In some embodiments, systems, apparatuses and methods are provided herein useful to obtain product information through scanning. In some embodiments, a method performed by a circuit and/or one or more processors comprises receiving, through an interface, data transaction requests from a local computing device on which the present embodiments are implemented, processing, by the present embodiments, the data transaction requests received through said interface; and completing said data transaction requests through a communication connection with a wide area network (WAN).

Some embodiments further comprise providing information to a third party recipient through processing functionality and/or programming of the present embodiments. Further, some embodiments comprise communicating, through the processing functionality, results of the processing to other portions of the present embodiments. Additionally or alternatively, some embodiments comprise providing, through the processing functionality, information useful in determining a nature of the data transaction request.

Some embodiments further comprise monitoring network access activity of the local computing device through monitoring circuitry and/or functionality of the present embodiments. In some instances, the network access activity comprises network activity of applications installed on the local computing device. Further, some embodiments comprise recording results of monitoring the network access activity within the processing functionality. The network activity comprises, in some embodiments, network activity from one or more of and/or a group consisting of http, https, network news transfer protocols, file sharing programs, file transfer protocols, chat room access, peer to peer chats, game protocols, downloads of data, and electronic mail activity. Further, some embodiments comprise completing the data transaction, by the present embodiments, through the interface.

In some embodiments, one or more of the circuitry and/or functionality may be implemented external to the present embodiments and/or the present embodiments may be implemented through distinct circuitry, processors and/or functionality. For example, in some implementations, the monitoring functionality may reside on the local computing device independent from the present embodiments, and be configured to send and receive data to the present embodiments. Accordingly, the spirit and scope of the present embodiments is not to be limited to the specific embodiments described.

While the invention has been described in conjunction with specific embodiments, it is evident that many alternatives, modifications and variations will be apparent to those skilled in the art in light of the foregoing description. Accordingly, the present invention attempts to embrace all such alternatives, modifications and variations that fall within the spirit and scope of the appended claims. Throughout this specification and the drawings and figures associated with this specification, numerical labels of previously shown or discussed features may be reused in another drawing figure to indicate similar features.

What is claimed is:

1. A method comprising:
   receiving, by a handheld patient device associated with a patient, a DICOM image associated with the patient and generated by a diagnostic device;
   encrypting, by the handheld patient device, the DICOM image, wherein the handheld patient device is one of a tablet computer and a smartphone; and
   transmitting, by the handheld patient device, the encrypted DICOM image to a medical professional device associated with a medical professional.

2. The method of claim 1, wherein the DICOM image is managed in a HIPAA-compliant manner.

3. The method of claim 2, further comprising linking, by the handheld patient device, the encrypted DICOM image to a unique patient identifier associated with the patient.

4. The method of claim 3, wherein the diagnostic device is configured to transmit the DICOM image to the handheld patient device via one of a wireless connection and a wired connection.

5. The method of claim 1, wherein the DICOM image is encrypted using a hypertext transfer protocol secure method.

6. The method of claim 1, wherein the diagnostic device is one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

7. The method of claim 1, wherein the medical professional device is remote from the handheld patient device.

8. A system comprising
   a handheld patient device associated with a patient, the handheld patient device being one of a tablet computer and a smartphone, and the handheld patient device comprising:
   data processing hardware; and
   memory hardware in communication with the data processing hardware, the memory hardware storing instructions that when executed on the data processing hardware cause the data processing hardware to perform operations comprising:
   receiving a DICOM image associated with the patient and generated by a diagnostic device;
   encrypting the DICOM image; and
   transmitting the encrypted DICOM image to a medical professional device associated with a medical professional.

9. The system of claim 8, wherein the DICOM image is managed in a HIPAA-compliant manner.

10. The system of claim 9, wherein the operations further comprise linking the encrypted DICOM image to a unique patient identifier associated with the patient.

11. The system of claim 8, wherein the DICOM image is encrypted using a hypertext transfer protocol secure method.

12. The system of claim 8, wherein the diagnostic device is configured to transmit the DICOM image to the data processing hardware of the handheld patient device via one of a wireless connection and a wired connection.

13. The system of claim 8, wherein the diagnostic device is one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

14. The system of claim 8, wherein the medical professional device is remote from the handheld patient device.

15. A tablet computer associated with a patient comprising:
   data processing hardware; and
   memory hardware in communication with the data processing hardware, the memory hardware storing instructions that when executed on the data processing hardware cause the data processing hardware to perform operations comprising:
   receiving a DICOM image associated with the patient and generated by a diagnostic device;
   encrypting the DICOM image; and
   transmitting the encrypted DICOM image to a medical professional device associated with a medical professional.

16. The tablet computer of claim 15, wherein the DICOM image is managed in a HIPAA-compliant manner.

17. The tablet computer of claim 16, wherein the operations further comprise linking the encrypted DICOM image to a unique patient identifier associated with the patient.

18. The tablet computer of claim 15, wherein the DICOM image is encrypted using a hypertext transfer protocol secure method.

19. The tablet computer of claim 15, wherein the data processing hardware is configured to receive the DICOM image from the diagnostic device via one of a wireless connection and a wired connection.

20. The tablet computer of claim 15, wherein the diagnostic device is one of an electrocardiograph (ECG), a pulse oximeter, a blood pressure cuff, a spirometer, a sphygmomanometer, a weight scale, a stethoscope, a blood chemistry analyzer, a microscope, an ultrasounds probe, a glucometer, a horoscope, a prothrombin time and international normalized ratio (PT/INR) machine, a medication station, an abdominal probe, a vascular access probe, an endocavity probe, an ophthalmology probe, a proscope, a thermometer, and a remotely-controlled 360 degree high definition camera.

* * * * *